United States Patent
Chan et al.

(10) Patent No.: US 10,719,574 B2
(45) Date of Patent: Jul. 21, 2020

(54) CALIBRATION OF A CHEST-MOUNTED WIRELESS SENSOR DEVICE FOR POSTURE AND ACTIVITY DETECTION

(71) Applicant: VITAL CONNECT, INC., San Jose, CA (US)

(72) Inventors: Alexander Chan, San Jose, CA (US); Nima Ferdosi, San Jose, CA (US); Ravi Narasimhan, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 126 days.

(21) Appl. No.: 15/864,030

(22) Filed: Jan. 8, 2018

(65) Prior Publication Data
US 2018/0189235 A1 Jul. 5, 2018

Related U.S. Application Data

(63) Continuation-in-part of application No. 15/459,017, filed on Mar. 15, 2017, now Pat. No. 10,317,427.
(Continued)

(51) Int. Cl.
| | |
|---|---|
| *G06F 17/00* | (2019.01) |
| *G07C 1/00* | (2006.01) |
| *G01P 21/00* | (2006.01) |
| *G04F 13/04* | (2006.01) |
| *A61B 5/11* | (2006.01) |

(Continued)

(52) U.S. Cl.
CPC .......... *G06F 17/00* (2013.01); *A61B 5/1116* (2013.01); *A61B 5/1118* (2013.01); *G01P 21/00* (2013.01); *G04F 13/04* (2013.01); *G07C 1/00* (2013.01); *A61B 5/00* (2013.01); *A61B 5/11* (2013.01); *A61B 5/6823* (2013.01); *A61B 2560/0223* (2013.01); *G01D 21/00* (2013.01);
(Continued)

(58) Field of Classification Search
CPC ........ G06F 17/00; G06F 17/40; A61B 5/1116; A61B 5/1118; G01P 21/00; G07C 1/00; G04F 13/04
See application file for complete search history.

(56) References Cited

U.S. PATENT DOCUMENTS

| | | |
|---|---|---|
| 6,044,297 A | 3/2000 | Sheldon et al. |
| 9,035,794 B2 | 5/2015 | Narasimhan et al. |

(Continued)

OTHER PUBLICATIONS

PCT International Search Report and Written Opinion of the International Searching Authority, dated Dec. 2, 2013, application No. PCT/US2013/045321.

*Primary Examiner* — Bryan Bui
(74) *Attorney, Agent, or Firm* — Brundidge & Stanger, P.C.

(57) ABSTRACT

A method and system for calibrating a wireless sensor device are disclosed. In a first aspect, the method comprises determining a vertical calibration vector and determining a rotation matrix using the vertical calibration vector to line up native axes of the wireless sensor device with body axes. In a second aspect, a wireless sensor device comprises a processor and a memory device coupled to the processor, wherein the memory device includes an application that, when executed by the processor, causes the processor to determine a vertical calibration vector and to determine a rotation matrix using the vertical calibration vector to line up native axes of the wireless sensor device with body axes.

5 Claims, 16 Drawing Sheets

Related U.S. Application Data which is a continuation of application No. 13/900,438, filed on May 22, 2013, now Pat. No. 9,632,981, which is a continuation-in-part of application No. 13/548,059, filed on Jul. 12, 2012, now Pat. No. 9,035,794.

(51) Int. Cl.
    *A61B 5/00*       (2006.01)
    *G06F 17/40*     (2006.01)
    *G01P 15/00*      (2006.01)
    *G01D 21/00*     (2006.01)
    *G06F 19/00*     (2018.01)

(52) U.S. Cl.
    CPC .............. *G01P 15/00* (2013.01); *G06F 17/40* (2013.01); *G06F 19/00* (2013.01)

(56) References Cited

U.S. PATENT DOCUMENTS

| | | | |
|---|---|---|---|
| 10,317,427 B2* | 6/2019 | Chan | ........................ G01P 21/00 |
| 2007/0115277 A1 | 5/2007 | Wang et al. | |
| 2010/0010583 A1 | 1/2010 | Panken et al. | |
| 2010/0298655 A1 | 11/2010 | McCombie et al. | |
| 2011/0172927 A1 | 7/2011 | Sahasrabudhe et al. | |
| 2011/0201969 A1 | 8/2011 | Hatlestad et al. | |
| 2011/0241656 A1 | 10/2011 | Piemonte et al. | |
| 2012/0101411 A1 | 4/2012 | Hausdorff et al. | |
| 2012/0203487 A1 | 8/2012 | Johnson | |
| 2013/0090881 A1 | 4/2013 | Janardhanan | |
| 2013/0274830 A1 | 10/2013 | Skelton | |
| 2014/0019080 A1 | 1/2014 | Chan | |
| 2017/0311116 A1* | 10/2017 | Aga | ......................... G08B 1/08 |

* cited by examiner

CALIBRATION OF A CHEST-MOUNTED WIRELESS SENSOR DEVICE FOR POSTURE AND ACTIVITY DETECTION

CROSS-REFERENCE TO RELATED APPLICATIONS

This application is a continuation-in-part of U.S. application Ser. No. 15/459,017, filed on Mar. 15, 2017, which is a continuation of U.S. application Ser. No. 13/900,438, filed on May 22, 2013, now U.S. Pat. No. 9,632,981, which is a continuation-in-part of U.S. application Ser. No. 13/548,059, filed on Jul. 12, 2012, now U.S. Pat. No. 9,035,794, the entire disclosures of which are incorporated herein by reference.

FIELD OF THE INVENTION

The present invention relates to wireless sensor devices, and more particularly, to calibration of a chest-mounted wireless sensor device for posture and activity detection.

BACKGROUND OF THE INVENTION

Wireless sensor devices are used in a variety of applications including the posture detection and activity monitoring of users. In many of these applications, a wireless sensor device is attached directly to the user's skin (e.g. near the chest area) to measure certain data. This measured data is then utilized for the posture detection and activity monitoring of the users.

Detecting posture from a patch form-factor chest-mounted wireless sensor device (e.g. accelerometer) is difficult if proper calibration is not performed. This is due to the fact that the patch can be worn in different positions making it difficult to distinguish postures if only non-calibrated accelerometer data is available. Therefore, there is a strong need for a cost-effective solution that overcomes the aforementioned issues. The present invention addresses such a need.

SUMMARY OF THE INVENTION

A method and system for calibrating a wireless sensor device are disclosed. In a first aspect, the method comprises determining a vertical calibration vector and determining a rotation matrix using the vertical calibration vector to line up native axes of the wireless sensor device with body axes.

In a second aspect, a wireless sensor device comprises a processor and a memory device coupled to the processor, wherein the memory device includes an application that, when executed by the processor, causes the processor to determine a vertical calibration vector and to determine a rotation matrix using the vertical calibration vector to line up native axes of the wireless sensor device with body axes.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION OF THE PREFERRED EMBODIMENT

Figure 1:
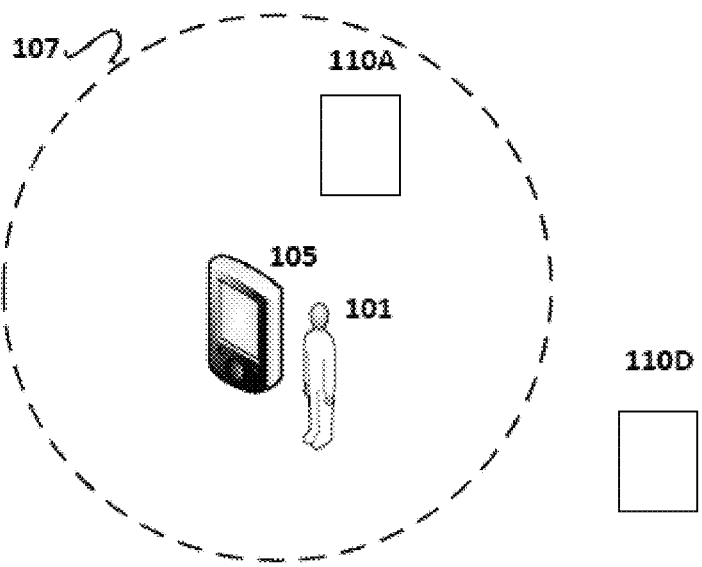
FIG. 1 illustrates an example system configuration for implementing one or more embodiments of identifying a roaming NFC device for a communicative connection.

The present invention relates to wireless sensor devices, and more particularly, to calibration of a chest-mounted wireless sensor device for posture and activity detection. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A relay may include an application manager that determines and/or detects a threshold value for a signal index for signals from proximately-located wireless sensor devices, upon initiation of an application on the relay; a wireless sensor device detector that, repeatedly, detects a signal from the respective proximately-located wireless sensor devices, and determines a signal index for the signal from the proximately-located wireless sensor devices; a wireless sensor device identifier that identifies those the proximately-located wireless sensor devices for which the determined signal index equals or exceeds the determined threshold value; and a wireless sensor device connector that communicatively connects the relay to one of the identified wireless sensor devices to calibrate the wireless sensor device via manual calibration.

A wireless sensor device that only utilizes non-calibrated accelerometer data leads to less accurate posture detection and activity level monitoring. Non-calibrated accelerometer data can be arbitrarily positioned relative to the actual body axes. Therefore, a calibration procedure of the wireless sensor device enables the generation of three derived axes of acceleration data that line up with actual body axes: anterior-posterior AP (front-to-back)—Z-axis; medial-lateral ML (left-to-right)—X-axis; and vertical VT (head-to-toe)—Y-axis. The calibration procedure requires determining at least the direction of the VT axis before the VT axis is then used to determine the other 2 axes. In another embodiment, additional calibration during leaning forward or lying supine is utilized to improve calibration accuracy.

A method and system in accordance with the present invention calibrates a wireless sensor device via automatic calibration, manual calibration, and sleep study calibration. In automatic calibration, an algorithm analyzes whether the user is walking and then obtains a vertical calibration vector during this detected walking period. In manual calibration, there is a wireless communication between the patch form-factor wireless sensor device and a relay (e.g. smartphone, handheld device, computer, communication device) that manually calibrates the wireless sensor device when selected or when automatic calibration fails. Manual calibration includes but is not limited to single upright calibration, walking calibration, upright and leaning forward calibration for improved accuracy, and supine and sitting up calibration for bedridden patients. In sleep study calibration, if only sleep data when the user is lying down is available (e.g. during a sleep study), an algorithm automatically calibrates the wireless sensor device given a whole night of data.

The calibration utilized by the method and system in accordance with the present invention enables a wireless communication between a wireless sensor device and a relay that manually calibrates the wireless sensor device. The wireless sensor device transmits a signal to the relay and if a signal index obtained from the transmitted signal equals or exceeds a threshold value, the wireless sensor device is determined to be within a predetermined proximity from the relay. The wireless sensor device for which the obtained signal index equals or exceeds a threshold value is identified and communicatively connected to the relay, and the connected wireless sensor device receives a Manual Calibration Request from the relay. Then, the wireless sensor device is calibrated via manual calibration.

The calibration utilized by the method and system in accordance with the present invention determines a vertical axis VT and uses the VT to determine the other 2 axes. If manual calibration is selected, all of the microelectromechanical systems (MEMS) based algorithms of the wireless sensor device utilize the manual calibration to detect posture and activity levels of the user. If automatic calibration is selected, all of the MEMS based algorithms of the wireless sensor device utilize the automatic calibration to detect posture and activity levels of the user. If neither manual calibration nor automatic calibration is selected, posture detection is disabled and all of the MEMS based algorithms of the wireless sensor device operate in non-calibrated mode.

Once automatic calibration of the wireless sensor device is achieved, the derived calibration vector enables the wireless sensor device to utilize various algorithms that measure the user's activity levels including but not limited to pedometer activity, fall detection, and posture detection. In one embodiment, after attaching the wireless sensor device to the user, the wireless sensor device continuously and automatically obtains varying types of data including but not limited to acceleration samples along an anteroposterior axis of the user. An application embedded within a processor of the wireless sensor device compares the acceleration samples to a threshold to measure the user's activity levels.

One of ordinary skill in the art readily recognizes that a variety of wireless sensor devices can be utilized including but not limited to a wireless sensor device in a patch form-factor, tri-axial accelerometers, uni-axial accelerometers, bi-axial accelerometers, gyroscopes, and pressure sensors and that would be within the spirit and scope of the present invention.

FIG. 1 shows an example system 100 configuration for implementing one or more embodiments of identifying a roaming device for a communicative connection.

In at least one example embodiment, system 100 may include relay 105 and wireless sensor devices 110A, 110B, 110C, and 110D.

Relay 105 may refer to a wireless processor-enabled device including, but not limited to a smartphone, handheld device, and a computer, etc., that is capable of hosting, initiating, and/or operating an application for which operation includes, in part, being communicatively connected, at least, to other similar wired or wireless devices, including but not limited to one or more of wireless sensor devices 110A, 110B, 110C, and 110D.

In at least on alternative embodiment, relay 105 may be a processor-enabled router, Wi-Fi hot-spot, or relay computer, e.g., notebook, laptop, smart phone, etc., that is communicatively connected individually or in tandem with one or more instances of wireless sensor devices 110.

Figure 4:
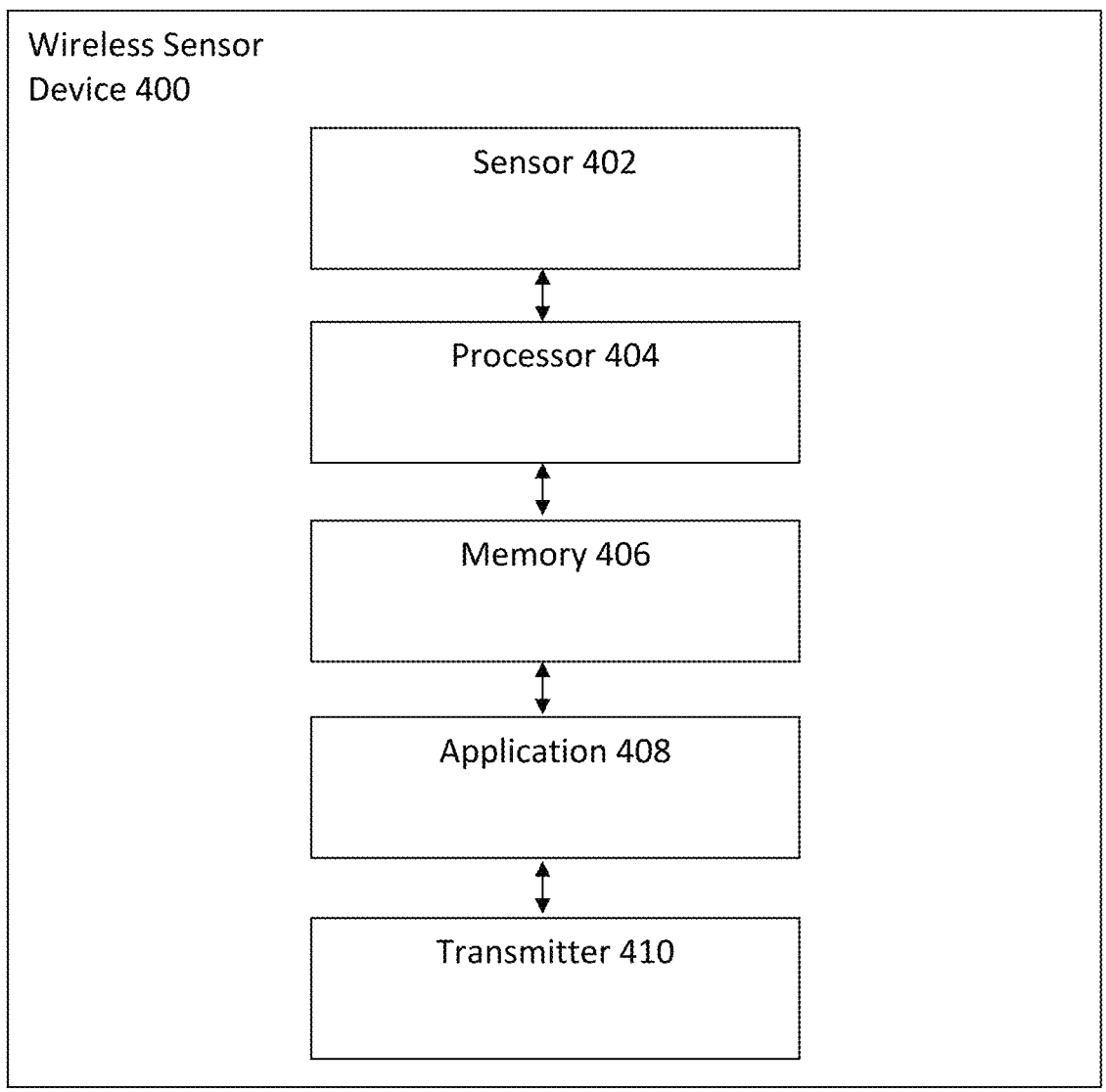
FIG. 4 illustrates a wireless sensor device in accordance with an embodiment.

Wireless sensor devices 110A, 110B, 110C, and 110D may also refer to a wireless processor-enabled device, that is capable of hosting, initiating, and/or operating for which operation includes, in part, being communicatively connected, at least, to other similar wired or wireless devices, including but not limited to relay 105. Example configuration of each wireless sensor devices 110A, 110B, 110C, and 110D are shown in FIG. 4. Each wireless sensor devices 110A, 110B, 110C, and 110D may refer to a wireless sensor device 400.

As set forth above, aspects of the disclosure may be arranged, substituted, combined, separated, and designed in a wide variety of different configurations, all of which are explicitly contemplated herein; thus, the quantity and even positioning of the wireless sensor devices in FIG. 1 is in no way representative or limiting of all contemplated embodiments of identifying a roaming device for a communicative connection. Thus, unless context otherwise requires, reference may be made herein to singular wireless sensor device 110 or plural wireless sensor devices 110.

In accordance with at least some implementations of identifying a roaming device for a communicative connection, relay 105 and one or more of wireless sensor devices 110 may be communicatively detectable relative to each other, at least antenna-to-antenna, via a communication link, which may include an NFC protocol, e.g., BLE. Thus, relay 105 may likely be capable of a communicative connection with an embodiment of wireless sensor devices 110 that is within a range of, e.g., 25 yards, or whatever range is in accordance with a current iteration of NFC technologies.

However, implementations of identifying a roaming device for a communicative connection are not limited to short-range protocols. Relay 105 and one or more of wireless sensor devices 110 may be communicatively detectable to each other, at least antenna-to-antenna, via a communication link that include various wireless networking and/or cellular technologies, such as LAN (Local Area Network), WAN (Wide Area Network), VAN (Value Added Network) or the like, or any one or more of known wireless networks, e.g., a mobile radio communication network, a satellite network, WiBro (Wireless Broadband Internet), Mobile WiMAX, HSDPA (High Speed Downlink Packet Access) or the like.

Common to the various communication protocols by which relay 105 and one or more of wireless sensor devices 110 may be connected, is a detectable received signal strength indication (hereafter "RSSI"), which is a measure of the power present in a radio signal between the communicating relay and wireless sensor device.

RSSI may be regarded as a relative received signal strength in a wireless environment, in arbitrary units. RSSI is an indication of the power level being received by relay 105 after antenna loss. Therefore, the higher the RSSI number, the stronger the signal and, presumably, the closer the embodiment of wireless sensor device 110 corresponding to the higher RSSI number is to relay 105.

There is no standardized relationship of any particular physical parameter to the RSSI reading. For example, the IEEE 802.11 standard does not define any relationship between RSSI value and power level in milliwatts or decibels. Thus, vendors and chipset makers provide their own accuracy, granularity, and range for the actual power (measured as milliwatts or decibels) and their range of RSSI values (from 0 to RSSI maximum). In accordance with some embodiments, RSSI is acquired during the preamble stage of receiving a data transmission frame, not over the full frame, e.g., upon initiation of an application on relay 105 and transmission therefrom.

Nevertheless, RSSI may have a correspondence to distance. Thus, in accordance with the example embodiment of FIG. 1, the threshold RSSI value for the application hosted, initiated, and/or operating on relay 105 may have a substantial correspondence to the distance represented by the transmission radius 107, of which relay 105 is the focal point. For example, if relay 105 is an NFC device, transmission radius may be one foot, i.e., twelve inches. Accordingly, in the example embodiment, only wireless sensor device 110A transmits a data frame to relay 105 that has an RSSI that meets or exceeds the determined threshold value; and, thus, only wireless sensor device 110A is identified as a candidate for a communicative connection with relay 105, via the respective instances of the same application running thereon.

Relay 105 may include an internal wireless networking card (not shown) to detect and measure the RSSI between relay 105 and any one of wireless sensor devices 110A, 110B, 110C, and 110D.

In accordance with at least some implementations of identifying a roaming device for a communicative connection, a connection manager corresponding to relay 105 may include an application manager that determines and/or detects a threshold value for a signal index, e.g., RSSI, for signals from wireless sensor devices 110, upon initiation of an application on the relay and, therefore, the preamble stage of receiving a data transmission frame. The connection manager may also include a wireless sensor device detector that determines the signal index from wireless sensor devices 110; and a wireless sensor device identifier that identifies those the proximately-located wireless sensor devices for which the determined signal index equals or exceeds the determined threshold value. That is, those embodiments of wireless sensor device 110 that do not even meet the determined threshold value are not identified for selection. The connection manager further includes a wireless sensor device connector that communicatively connects relay 105 to at least one embodiment of identified wireless sensor device 110, preferably that having the strongest RSSI, for implementing communication between the devices via the respective instances of the particular application running on both devices.

In some embodiments, selection of wireless sensor device 110 is automated; while in others, the selection is user-implemented. Thus, in the former embodiments, only those wireless sensor devices for which the RSSI meets or exceeds the threshold value, may be eligible for communicative connection to relay 105; whereas in the latter embodiments, only those wireless sensor devices for which the RSSI meets or exceeds the threshold value are even identified, e.g., for the user of relay 105 to select.

Figure 2:
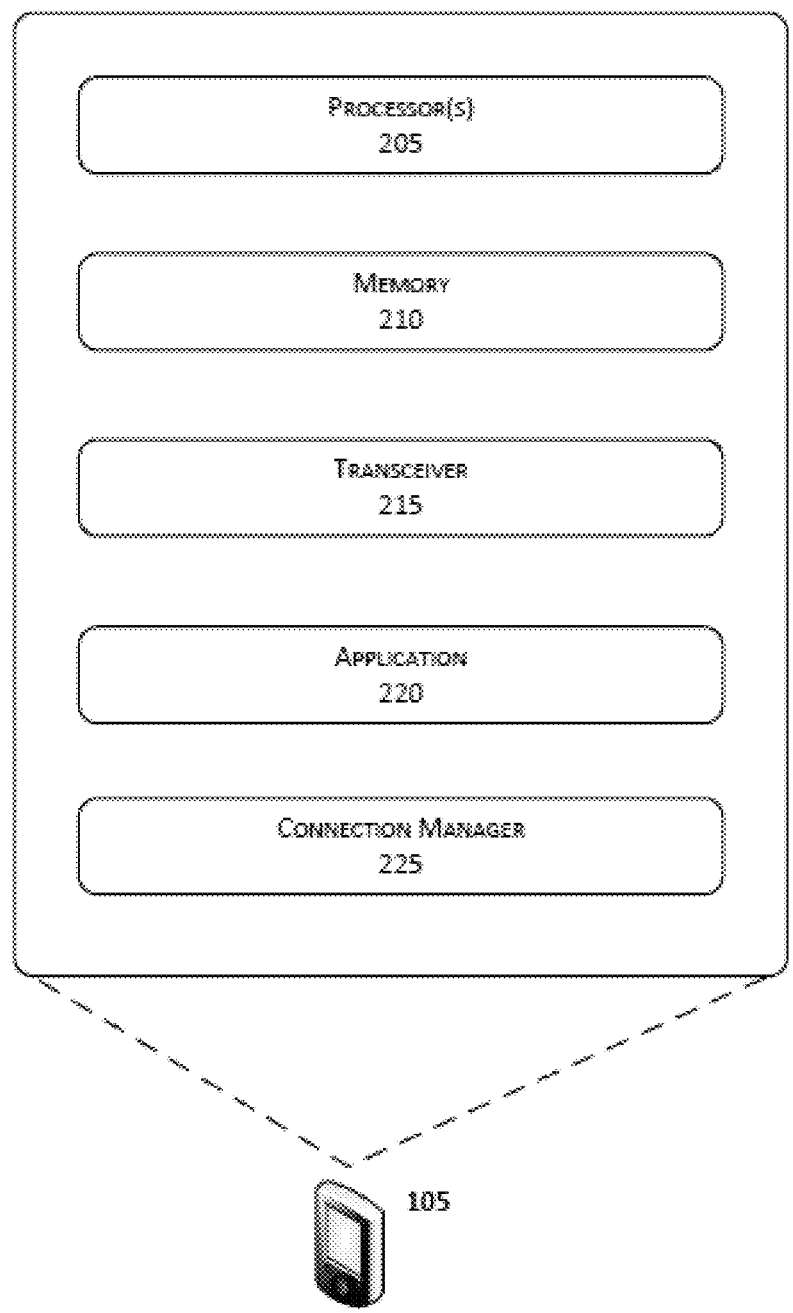
FIG. 2 illustrates an example configuration of a relay by which aspects of identifying a roaming device for a communicative connection may be implemented.

FIG. 2 shows an example configuration of a relay by which aspects of identifying a roaming device for a communicative connection may be implemented.

As depicted, relay 105 may include one or more processors 205, memory 210, transceiver 215, application 220, and connection manager 225. Although illustrated as discrete components, these various components may be divided into additional components, combined into fewer components, or eliminated altogether while being contemplated within the scope of the disclosed subject matter. Further, it will be understood by those of ordinary skill in the art that each example component may be implemented, individually and/or collectively, by a wide range of hardware, software, firmware, or virtually any combination thereof.

Processor(s) 205 may refer to one or more processors that enable the functionality of the various components of relay 105. Processors(s) 210 may be deployed singularly or as a plurality thereof, depending on processing capabilities and/or requirements of the remaining components of relay 105.

Memory 210 may refer to one or more storage components that may be designed, programmed, and/or configured to store, at least temporarily, signal strength index data. In at least some embodiments of relay 105, the storage capacity of memory 210 may be commensurate with a size of relay 105 and/or processing power of processor(s) 205.

Transceiver 215 may refer to one or more executable components that may be designed, programmed, and/or configured as a transmitter to transmit and even receive data utilizing an NFC protocol, e.g., including, but not limited to, BLE, or, at least antenna-to-antenna, via a communication link that include various wireless networking and/or cellular technologies, such as LAN (Local Area Network), WAN (Wide Area Network), VAN (Value Added Network) or the like, or any one or more of known wireless networks, e.g., a mobile radio communication network, a satellite network, WiBro (Wireless Broadband Internet), Mobile WiMAX, HSDPA (High Speed Downlink Packet Access) or the like.

Further, transceiver 225 may be designed, programmed, and/or configured as a receiver to receive a data frame, upon initiation of application 220, from proximately-located embodiments of wireless sensor device 110.

Application 220 may refer to an executable program that is hosted, initiated, and/or operated on relay 105, as well as on wireless sensor devices 110. Embedded within application 220 is a threshold signal strength index value, e.g., RSSI, or a link to such value that is stored on memory 210.

Connection manager 225 may refer to an executable component that is designed, programmed, and/or configured to determine the threshold signal strength index value, e.g., RSSI, for application 220 on relay 105 and one or more of wireless sensor devices 110; and identify, for a communicative connection, only those embodiments of wireless sensor devices 110 for which the signal strength index value, relative to relay 105, meets or exceeds the threshold value, all upon initiation of application 220 on relay 105 and/or upon receiving an initial data frame from any of wireless sensor devices 110.

Figure 3:
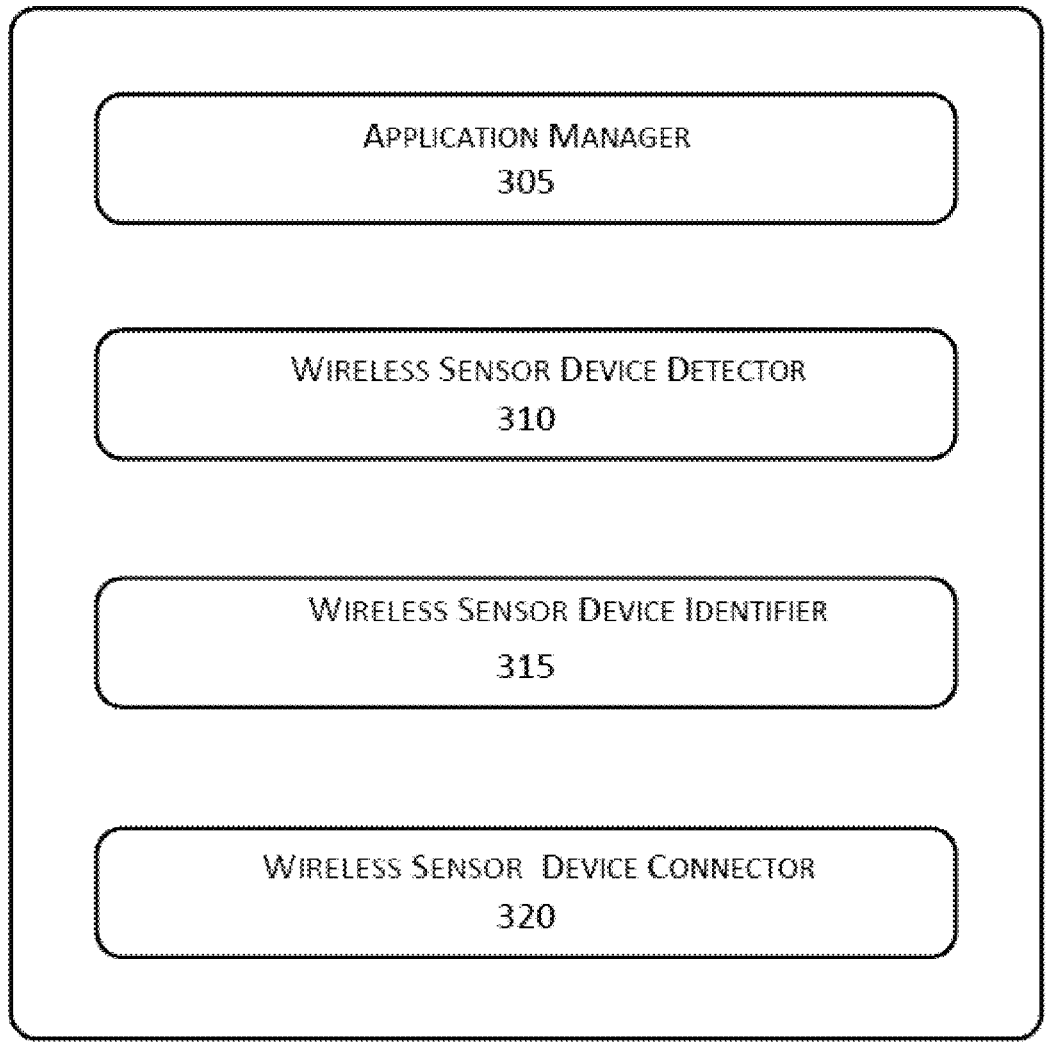
FIG. 3 illustrates an example configuration of a connection manager by which aspects of identifying a roaming device for a communication connection may be implemented.

FIG. 3 shows an example configuration of connection manager 225 by which aspects of identifying a roaming device for a communicative connection may be implemented.

As depicted, connection manager may include application manager 305, wireless sensor device detector 310, wireless sensor device identifier 315, and wireless sensor device 320. Although illustrated as discrete components, these various components may be divided into additional components, combined into fewer components, or eliminated altogether while being contemplated within the scope of the disclosed subject matter. Further, it will be understood by those of ordinary skill in the art that each example component may be implemented, individually and/or collectively, by a wide range of hardware, software, firmware, or virtually any combination thereof.

Application manager 305 may refer to an executable component of connection manager 225 that may be designed, programmed, and/or configured to determine a threshold value for a signal strength index, e.g., RSSI, that is embedded in application 220 or for which a link to the value, stored on memory 210, is embedded in application 220. The threshold value may be deemed to be the minimum signal strength index value, e.g., RSSI, required for wireless sensor device 110 to be identified as a candidate for a communicative connection to relay 105, via application 220.

Wireless sensor device detector 310 may refer to an executable component of connection manager 225 that may be designed, programmed, and/or configured to detect an initial data frame from wireless sensor device 110 upon initiation of application 220 on relay 105; and, further, determine the actual signal strength index value corresponding to the detected initial data frame. Wireless sensor device detector 310 may perform iterations of such detection and determination repeatedly, as initial data frames are received from various embodiments of wireless sensor device 110, or on a predetermined time basis, e.g., 1 sec.

Wireless sensor device identifier 315 may refer to an executable component of connection manager 225 that may be designed, programmed, and/or configured to determine whether the detected signal strength index, e.g., RSSI, for the detected initial data frame meets or exceeds the determined threshold value.

If relay 105 is, e.g., a Wi-Fi hotspot, and therefore connection to a wireless sensor device is automated, wireless sensor device identifier 315 may be designed, programmed, and/or configured to prohibit communicative connection to an embodiment of wireless sensor device 110 for which the detected signal strength index, e.g., RSSI, does not at least meet the threshold value that is embedded in application 220 or stored in memory 210.

Accordingly, since not all embodiments of wireless sensor device 310 are labeled or otherwise identified to relay 105, and because often multiple embodiments of wireless sensor device 110 are physically eligible for communicative connection to relay 105, when relay 105 scans for a wireless sensor device to connect, myriad wireless sensor devices may be deemed eligible for connection. Thus, wireless sensor device identifier may be utilized to limit the number of wireless sensor devices to which relay 105 may communicatively connect, or otherwise make selection of a partner device more easily managed.

If relay 105 is a mobile device for which connection to a wireless sensor device is manually activated by, e.g., user 101, wireless sensor device identifier 315 may be designed, programmed, and/or configured to display an identifier only for those embodiments or wireless sensor device 110 for which the detected signal strength index, e.g., RSSI, meets or exceeds the threshold value that is embedded in application 220 or stored in memory 210. In addition, or alternatively, wireless sensor device 315 may also be designed, programmed, and/or configured to prohibit communicative connection to an embodiment of wireless sensor device 110 for which the detected signal strength index does not at least meet the threshold value.

Wireless sensor device connector 320 may refer to an executable component of connection manager 225 that may be designed, programmed, and/or configured to communicatively connect relay 105 to one or more embodiments of wireless sensor device 110 for which the detected signal strength index, e.g., RSSI, at least meets the threshold value that is embedded in application 220 or stored in memory 210, as determined by wireless sensor device identifier 315; and, further, transmit a Manual Calibration Request to one or more embodiments of wireless sensor device 110 for which the detected signal strength index, e.g., RSSI, at least meets the threshold value that is embedded in application 220 or stored in memory 210, as determined by wireless sensor device identifier 315.

Wireless sensor device identifier 315 may further refer to an executable component of connection manager 225 that may be designed, programmed, and/or configured to identify a location of one or more embodiments of wireless sensor device 110 for which the detected signal strength index, e.g., RSSI, at least meets the threshold value that is embedded in application 220 or stored in memory 210, as determined by wireless sensor device identifier 315. Then, a Manual Calibration Request is transmitted to the wireless sensor device 110 based on the location of the wireless device. Different types of Manual Calibration Requests are transmitted to the wireless sensor device 110 based on the location of the wireless device.

FIG. 4 illustrates a wireless sensor device 400 in accordance with an embodiment. The wireless sensor device 400 includes a sensor 402, a processor 404 coupled to the sensor 402, a memory 406 coupled to the processor 404, an application 408 coupled to the memory 406, and a transmitter 410 coupled to the application 408. In one embodiment, the wireless sensor device 400 is attached, in any orientation to a user and on any location of the user. In another embodiment, the wireless sensor device 400 is chest-mounted to the user. The sensor 402 obtains data from the user and transmits the data to the memory 406 and in turn to the application 408. The processor 104 executes the application 408 to monitor information regarding the user's posture and activity levels. The information is transmitted to the transmitter 410 and in turn relayed to another user or device.

In one embodiment, the sensor 402 is a microelectromechanical system (MEMS) tri-axial accelerometer and the processor 404 is a microprocessor. One of ordinary skill in the art readily recognizes that a variety of devices can be utilized for the processor 404, the memory 406, the application 408, and the transmitter 410 and that would be within the spirit and scope of the present invention.

A wireless sensor device 400 may also be capable of hosting, initiating, and/or operating for which operation includes, in part, being communicatively connected, at least, to other similar wired or wireless devices, including but not limited to relay. The wireless sensor device 400 may be configured to transmit a signal to a relay 105. For example, the wireless sensor device 400 transmits a beacon signal via short range wireless connectivity standard protocol, e.g., BLE. The beacon signal represents signal requesting a communicative connection to one or more instances of relay that are within range for a communicative connection.

To describe the features of the present invention in more detail, refer now to the following description in conjunction with the accompanying Figures.

Automatic Calibration:

The wireless sensor device can be automatically calibrated utilizing an acceleration vector corresponding to the footsteps of the user while walking. Automatic calibration starts after the wireless sensor device is powered on and is attached to the body of the user (typically the chest area). During a predetermined time period (e.g. the first fifteen minutes) after the attachment of the wireless sensor device, an acceleration vector corresponding to the footsteps of the user is detected and is utilized to calculate a calibration vector. If during the predetermined time period, at least a predetermined number of steps (e.g. 25 steps) by the user are not detected, the automatic calibration process is terminated and the MEMS based algorithms of the wireless sensor device operate in the non-calibrated mode.

In one embodiment, the automatic calibration process is repeated every time the wireless sensor device patch is applied to the skin of the user to ensure correct calibration in use-cases when the user changes position of the patch without power-cycling it. In another embodiment, the automatic calibration process and resulting calibration vector is given less priority than any form of manual calibration and the calibration vector derived from any form of manual calibration overrides the calibration vector derived from automatic calibration.

In order to accurately detect when the user is walking for the automatic calibration, a walking detection algorithm that does not depend on the calibration is utilized by the wireless sensor device to determine when the user is walking for the step count. In one embodiment, the walking detection algorithm comprises: retrieving a predetermined time period window (e.g. 1 second) of raw accelerometer data in the 3 axes (x, y, z), computing the signal magnitude area (SMA) for the predetermined time period window, computing the magnitude of acceleration in the horizontal plane ($mag_{horz}$) and overall (man) and comparing the calculated SMA and magnitude of accelerations to various thresholds.

Figure 5:
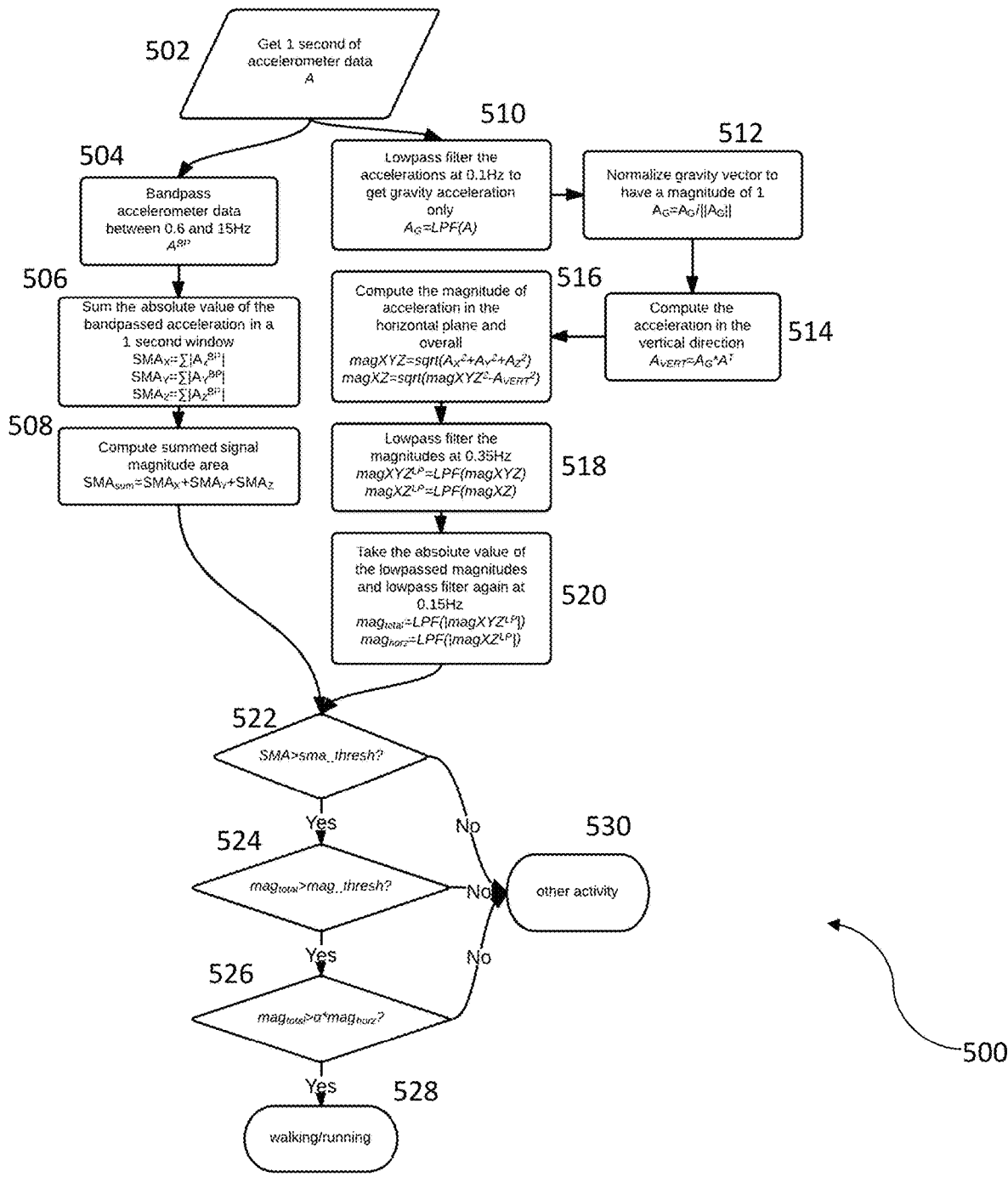
FIG. 5 illustrates a method of a wireless sensor device utilizing a walking detection algorithm in accordance with an embodiment.

FIG. 5 illustrates a method 500 for a wireless sensor device utilizing a walking detection algorithm in accordance with an embodiment. In the method 500, the wireless sensor device retrieves 1 second of raw accelerometer data in the 3 axes (x, y, z), via step 502. To calculate the signal magnitude area (SMA) for the 1 second window, the wireless sensor device bandpass filters a signal, detected by the wireless sensor device, between 0.6 Hz and 15 Hz to derive $A^{BP}$, via step 504, sums an absolute value of the filtered signal for the 1 second window where $SMA_X=\Sigma|A_X^{BP}|$, $SMA_Y=\Sigma|A_Y^{BP}|$, $SMA_Z=\Sigma|A_Z^{BP}|$, via step 506, and sums the results for each of the 3 axes to get an overall $SMA_{sum}$ value where $SMA_{sum}=SMA_X+SMA_Y+SMA_Z$, via step 508.

To calculate the magnitude of acceleration in the horizontal plane ($mag_{horz}$) and overall ($mag_{total}$), the wireless sensor device lowpass filters the raw acceleration at 0.1 Hz to derive a gravity component $A_G$ where $A_G=LPF(A)$, via step 510, normalizes the gravity component to derive a magnitude of 1, where $A_G=A_G/\|A_G\|$, via step 512, calculates an acceleration in a vertical direction $A_{VERT}$, where $A_{VERT}=A_G*A^T$, via step 514, calculates an overall magnitude of acceleration as $magXYZ=sqrt(A_X^2+A_Y^2+A_Z^2)$ and and a magnitude of acceleration in the horizontal plane as $magXZ=sqrt(magXYZ^2-A_{VERT}^2)$, via step 516, lowpass filters the magnitudes derived in step 516 at 0.35 Hz to derive $magXYZ^{LP}$ and $magXZ^{LP}$, via step 518, and takes an absolute value of the lowpass magnitudes derived in step 518 and lowpass filter again at 0.15 Hz to derive $mag_{total}=LPF(|magXYZ^{LP}|)$ and $mag_{horz}=LPF(|magXZ^{LP}|)$, via step 520.

After computing the SMA and the magnitude of acceleration in both the horizontal plane and overall, the wireless sensor device analyzes whether SMA is greater than a threshold sma_thresh, via step 522. If yes (SMA>sma_thresh), the wireless sensor device analyzes whether $mag_{total}$ is greater than a threshold mag_thresh via step 524. If yes ($mag_{total}$>mag_thresh), the wireless sensor device analyzes whether $mag_{total}$ is greater than the $mag_{horz}$ times a constant α (e.g. α=1), via step 526. If yes ($mag_{total}$>α*$mag_{horz}$), then the wireless sensor device classifies the current time and activity as walking, via step 528. If any of steps 522-556 are not met, then the wireless sensor device classifies the current time and activity as another activity, via step 530.

Figure 6:
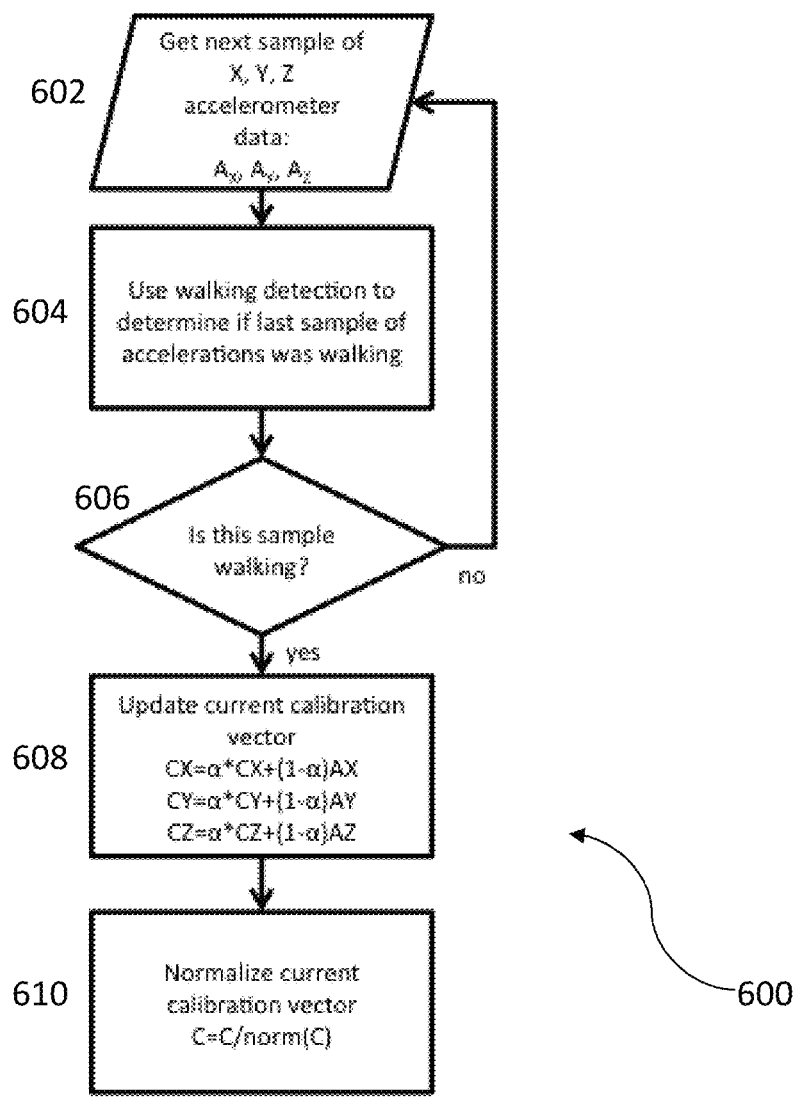
FIG. 6 illustrates a method for adaptive calibration in accordance with an embodiment.

Adaptive Calibration:

Occasionally, the implicit/automatic calibration based on walking is inaccurate and confuses another activity for walking. In this case, the wireless sensor device 400 utilizes adaptive calibration to correct for incorrect calibrations over time. The wireless sensor device 400 analyzes periods of walking and slowly adjusts the calibration vector over time. The calibration vector is adjusted by adding a small amount of the current acceleration during walking and renormalizing each time. FIG. 6 illustrates a method 600 for adaptive calibration in accordance with an embodiment.

In the method 600, a wireless sensor device retrieves a next sample of x, y, z accelerometer data ($A_X$, $A_Y$, $A_Z$), via step 602, and utilizes walking detection to determine if a last sample of accelerometer data/accelerations was walking, via step 604. If the wireless sensor device determines that the last sample is of walking, via step 606, the current calibration vector is updated per $CX=\alpha*CX+(1-\alpha)A_X$, $CY=\alpha*CY+(1-\alpha)A_Y$, $CZ=\alpha*CZ+(1-\alpha)A_Z$, via step 608. To complete the adaptive calibration, the wireless sensor device normalizes the current calibration vector per C=C/norm(C), via step 610.

In the adaptive calibration, α is a parameter that determines how slowly the calibration vector is adjusted (e.g. the closer to 1, the slower the adaptation). In one embodiment, the value of α=0.999973 resulting in a time-constant of 10 minutes for a sampling rate of 62.5 Hz.

Manual Calibration:

The wireless sensor device can also be manually/explicitly calibrated utilizing a variety of methodologies including but not limited to a manual calibration based on the user's upright position, a manual calibration based on walking/taking steps, and a manual calibration based on a bedridden user. During explicit calibration, the user, through an interface like a relay (e.g. smartphone) or through a predefined protocol (e.g. standing upright at the time of attaching the patch form-factor wireless sensor device to the user), informs the wireless sensor device of his/her posture.

The calibration vector acquired through the latest manual calibration will override the calibration vector derived from automatic calibration and earlier manual calibrations of the same type. Manual calibration requires an interaction between the user and the relay as well as the relay and the wireless sensor device. Bedridden users incapable of standing upright will go through two steps of calibration based on leaning-back and lying down flat in supine postures.

Figure 7:
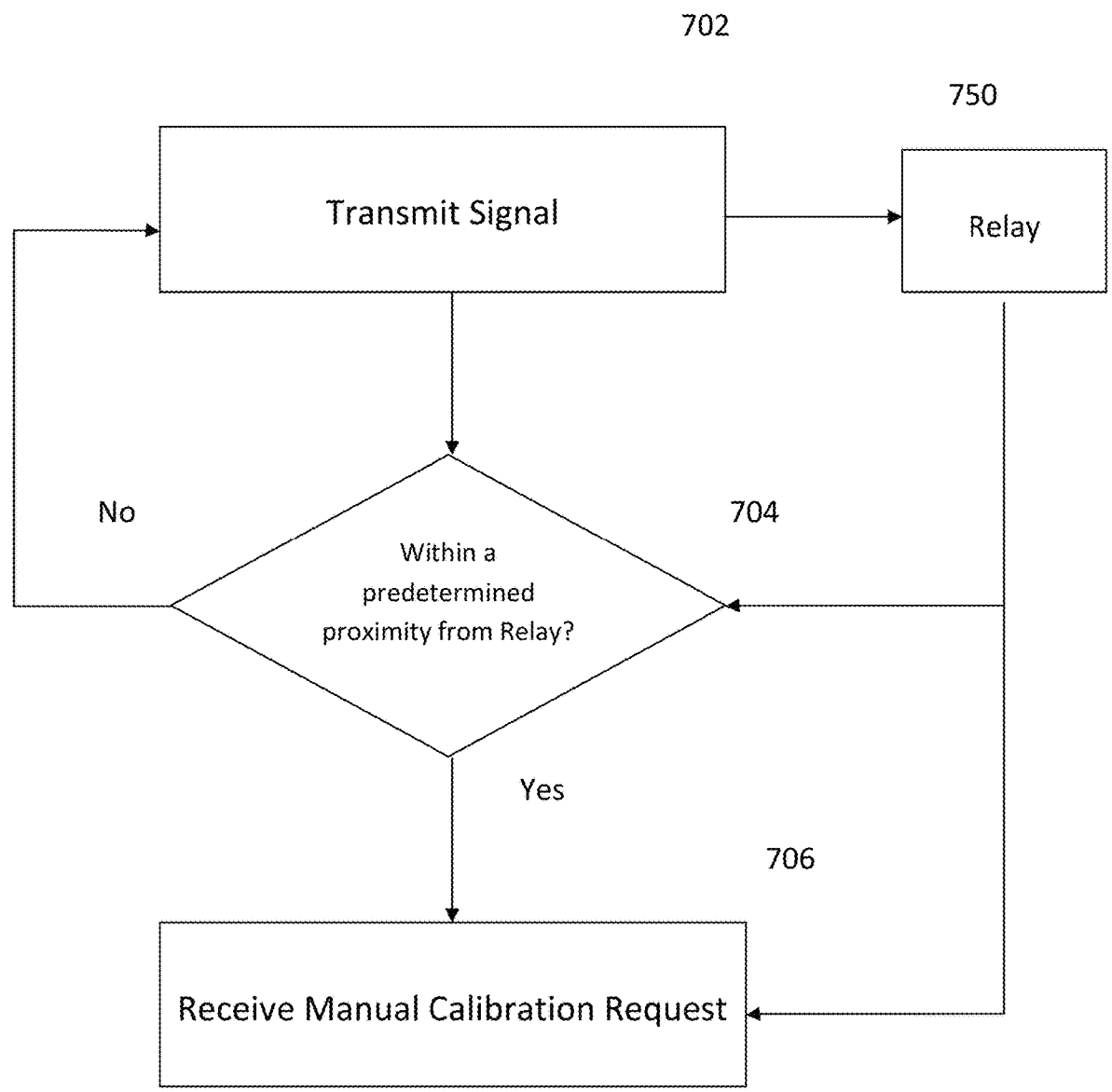
FIG. 7 illustrates a method of a wireless sensor device connecting a relay for manual calibration in accordance with an embodiment.

FIG. 7 illustrates a method 700 of a wireless sensor device to connect a relay for manual calibration in accordance with an embodiment. In the method, a wireless sensor device transmits a signal to a relay 750, via step 702. The relay 750 may refer to a relay 105. For example, the wireless sensor device transmits a beacon signal via short range wireless connectivity standard protocol, e.g., BLE. The beacon signal represents signal requesting a communicative connection to one or more instances of relay that are within range for a communicative connection.

A wireless sensor device is determined to be within a predetermined proximity from a relay 750 if a signal index obtained from the transmitted signal equals or exceeds a threshold value via step 704. The relay 750 may determine the wireless sensor is within a predetermined proximity from the relay 750 if a signal index obtained from the transmitted signal equals or exceeds a threshold value. In one embodiment, the signal index is a measure of a received signal strength indicator (RSSI) between a relay and the wireless sensor device. Alternatively, the signal index is a received channel power indicator. The wireless sensor device for which the obtained signal index equals or exceeds a threshold value is identified and communicatively connected to the relay 750 and the connected wireless sensor device receives a Manual Calibration Request from the relay 750 via step 706.

Examples of the types of Manual Calibration Requests received from a relay include but are not limited to an upright manual calibration request, a walking manual calibration request, and a bedridden user manual calibration request. Based on a received type of the Manual Calibration Request, one of upright manual calibration, manual calibration based on walking, or manual calibration of a bedridden user is performed in accordance with one of following descriptions regarding FIGS. 8-10. The types of Manual Calibration Requests are inputted via a relay or smartphone application by the user of the wireless sensor device.

In one embodiment, after a determination that a wireless sensor device is within a predetermined proximity from a relay if a signal index obtained from the transmitted signal equals or exceeds a threshold value via step 704, a location of the wireless sensor device is determined. Then, the wireless sensor device receives a Manual Calibration Request from the relay based on the location of the wireless device. For example, the location associated with the wireless sensor device includes patient rooms, hallways, physical therapy rooms, X-ray rooms, operating rooms, or similar rooms in a hospital building. If the location of the wireless sensor device is determined as a physical therapy room, the wireless sensor device receives a request for upright manual calibration. If the location of the wireless sensor device is determined as a patient room, the wireless sensor device receives a request for manual calibration of a bedridden user. As shown in the above non-limiting examples, the wireless sensor device receives different types of Manual Calibration Requests based on the location. Based on a received type of the Manual Calibration Request, one of upright manual calibration, manual calibration based on walking, or manual calibration of a bedridden user is performed in accordance with one of following descriptions regarding FIGS. 8-10.

Figure 8:
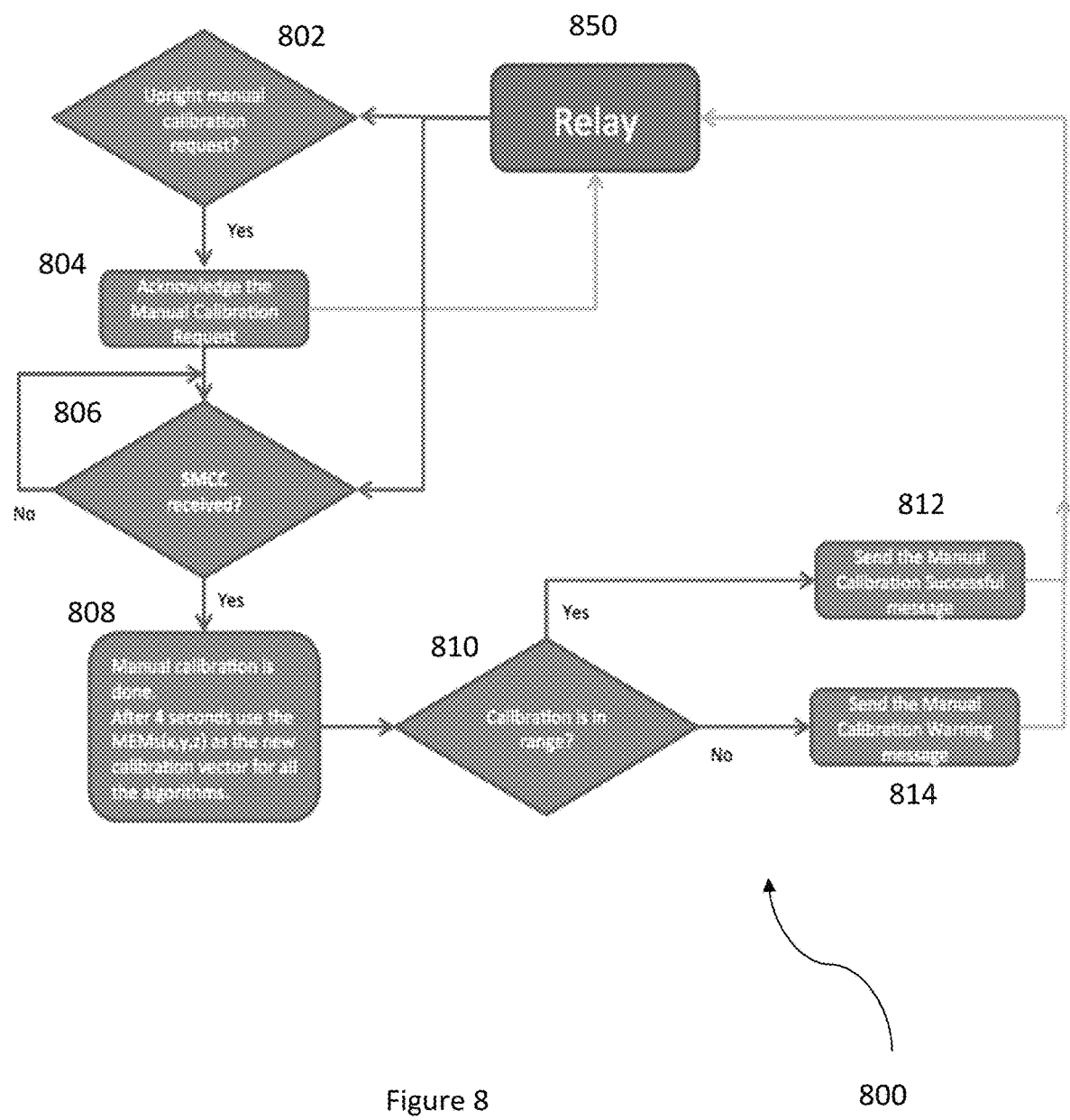
FIG. 8 illustrates a method for upright manual calibration in accordance with an embodiment.

FIG. 8 illustrates a method 800 for upright manual calibration in accordance with an embodiment. In the method 800, a wireless sensor device receives a Manual Calibration Request from the user based upon a standing upright position, via step 802, and acknowledges the receipt of the Manual Calibration Request, via step 804. After receiving the Manual Calibration Request from the user, the wireless sensor device waits for a predetermined time period (e.g. 4 seconds) to receive a Start Manual Calibration Command (SMCC) from a relay 850, via step 806.

In one embodiment, the relay 850 is a communication device including but not limited to a smartphone, handheld device, and a computer. The relay 850 may refer to a relay 105. After receiving the Start Manual Calibration Command, the wireless sensor device determines a New Upright Calibration Vector and waits for another predetermined time period (e.g. 4 seconds) before replacing the Current Upright Calibration Vector with the New Upright Calibration Vector that is a lowpass filtered MEMS vector (x, y, z), via step 808.

The calibration is within range if the angle of the New Upright Calibration Vector versus the vertical axis of the wireless sensor device is less than 30 degrees. The wireless sensor device determines whether the calibration is within range, via step 810. If yes (the calibration is within range), then the wireless sensor device transmits a Manual Calibration Success status to the relay 850, via step 812. If no (the calibration is not within range), then the wireless sensor device transmits a Manual Calibration Warning status to the relay 850, via step 814.

In one embodiment, after the upright calibration is performed, an additional calibration is performed on the wireless sensor device to improve the accuracy of the calibration. In the additional calibration, the user is instructed to bend over and remain in this position for a predetermined time period (e.g. 5 seconds) to provide a second calibration vector which improves the overall calibration. The second calibration vector allows for an exact determination of the medial-lateral (ML) and anteroposterior (AP) axes, as opposed to an estimate if provided with only a single upright calibration.

FIG. 8 illustrates a method 900 for manual calibration based on walking in accordance with an embodiment. In the method 900, a wireless sensor device receives a Manual Calibration Request from the user based on walking/taking steps, via step 902, and acknowledges the receipt of the Manual Calibration Request, via step 904. After receiving the Manual Calibration Request from the user, the wireless sensor device waits for a predetermined time period (e.g. 4 seconds) to receive a Start Manual Calibration Command (SMCC) from a relay 950, via step 906.

In one embodiment, the relay 950 is a communication device including but not limited to a smartphone, handheld device, and a computer. The relay 950 may refer to a relay 105. After receiving the Start Manual Calibration Command, the wireless sensor device utilizes the first predetermined number of steps (e.g. the first 20 steps) to calculate a New Upright Calibration Vector, via step 908.

The wireless sensor device determines whether the predetermined number of steps have been detected within a predetermined time period (e.g. 60 seconds) after receiving the SMCC (the start of the calibration), via step 910. If yes, the manual calibration is completed and the wireless sensor device replaces the Current Upright Calibration Vector with the New Upright Calibration Vector for utilization by the MEMS algorithms, via step 912. If no, the manual calibration is not completed and the status of the calibration does not change and the Current Upright Calibration Vector is maintained and not replaced by the New Upright Calibration Vector which is instead discarded, via step 916.

The wireless sensor device also determines whether the calibration is within range. The calibration is within range if the angle of the New Upright Calibration Vector versus the vertical axis of the wireless sensor device is less than 30 degrees. Based upon step 910 and the determination of whether the calibration is within range, the wireless sensor device transmits a manual calibration status message to the relay 950.

A Manual Calibration Success status is transmitted to the relay 950, via step 914, if at least the predetermined number of steps is detected within the predetermined time period after the start of the calibration per step 910 and the calibration is within range. A Manual Calibration Warning status is transmitted to the relay 950 if at least the predetermined number of steps is detected within the predetermined time period after the start of the calibration per step 910 but the calibration is not within range.

In the cases of a "success" and "warning" message, the wireless sensor device updates the calibration vector with the New Upright Calibration Vector that replaces the Current Upright Calibration Vector. A Manual Calibration Failure status is transmitted to the relay 950, via step 918, if at least the predetermined number of steps is not detected within the predetermined time period after the start of the calibration per step 910. In the case of a "failure" message, the wireless sensor device does not update the calibration vector and so the Current Upright Calibration Vector is not replaced.

Figure 10:
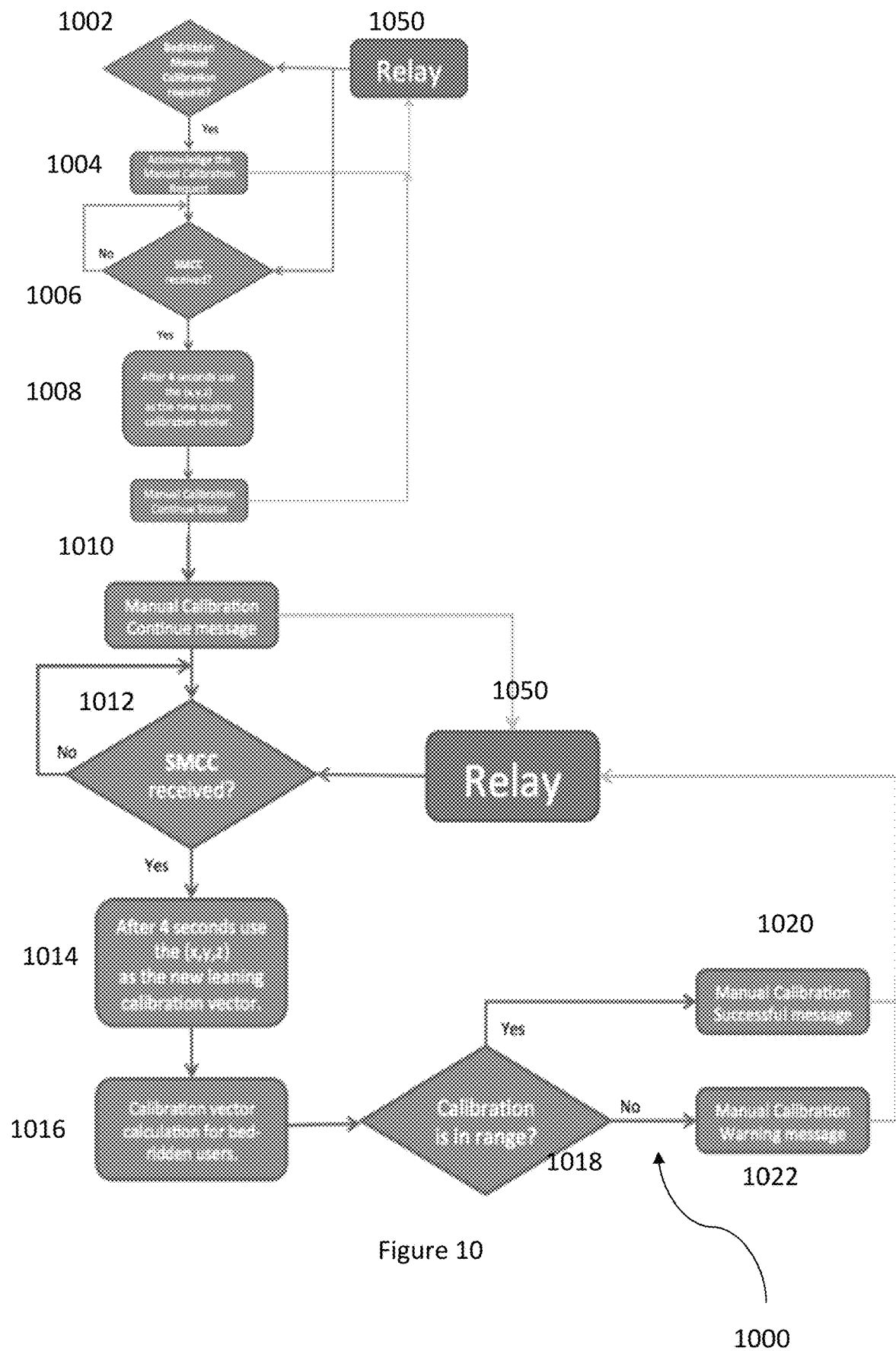
FIG. 10 illustrates a method for manual calibration of a bedridden user in accordance with an embodiment.

FIG. 10 illustrates a method 1100 for manual calibration of a bedridden user in accordance with an embodiment. In the method 1100, a wireless sensor device receives a Manual Calibration Request from the bedridden user or another user (e.g. nurse, assistant), via step 1002, and acknowledges the receipt of the Manual Calibration Request, via step 1004. After receiving the Manual Calibration Request from the user, the wireless sensor device waits for a first predetermined time period (e.g. 4 seconds) to receive a first Start Manual Calibration Command (SMCC) from a relay 1050, via step 1006.

In one embodiment, the relay 1050 is a communication device including but not limited to a smartphone, handheld device, and a computer. The relay 1050 may refer to a relay 105. After receiving the first Start Manual Calibration Command, the wireless sensor device waits for a second predetermined time period (e.g. 4 seconds) before replacing the Current Supine Calibration Vector with a New Supine Calibration Vector that is a lowpass filtered MEMS vector (x, y, z) determined while the user is flat on his/her back, via step 1008.

The wireless sensor device sends a Manual Calibration Continue status message to the relay 1050, via step 1010, and waits for a third predetermined time period (e.g. 4 seconds) to receive a second Start Manual Calibration Command (SMCC) from the relay 1050, via step 1012. After receiving the second Start Manual Calibration Command, the wireless sensor device waits for a fourth predetermined time period (e.g. 4 seconds) before replacing the Current Leaning Calibration Vector with a New Leaning Calibration Vector that is a lowpass filtered MEMS vector (x, y, z) determined while the user is in a slightly raised position on his/her back, via step 1014.

The wireless sensor device calculates the calibration vector for the bedridden user, via step 1016, and then determines whether the calibration based on both leaning back and supine calibrations is within range, via step 1018.

The calibration is within range if the angle of the New Leaning Calibration Vector versus the vertical axis of the wireless sensor device is less than 30 degrees and if the angle of the New Supine Calibration Vector versus the vertical axis of the wireless sensor device is less than 30 degrees. If yes (calibration is within range), the wireless sensor device sends a Manual Calibration Success status message to the relay 1050, via step 1020, and if no (calibration is not within range), the wireless sensor device sends a Manual Calibration Warning status message to the relay 1050, via step 1022.

Therefore, the types of Manual Calibration Requests inputted via a relay or smartphone application by the user of the wireless sensor device include but are not limited to an upright manual calibration request, a walking manual calibration request, and a bedridden user manual calibration request. After receiving and acknowledging one of these types of requests, the wireless sensor device waits to receive the SMCC once the user has received various instructions and is ready for the calibration to begin (e.g. is in the correct position). After receiving the SMCC, the wireless sensor device performs the requested method of calibration and sends the manual calibration status messages to the relay which informs the user of the status message.

Figure 9:
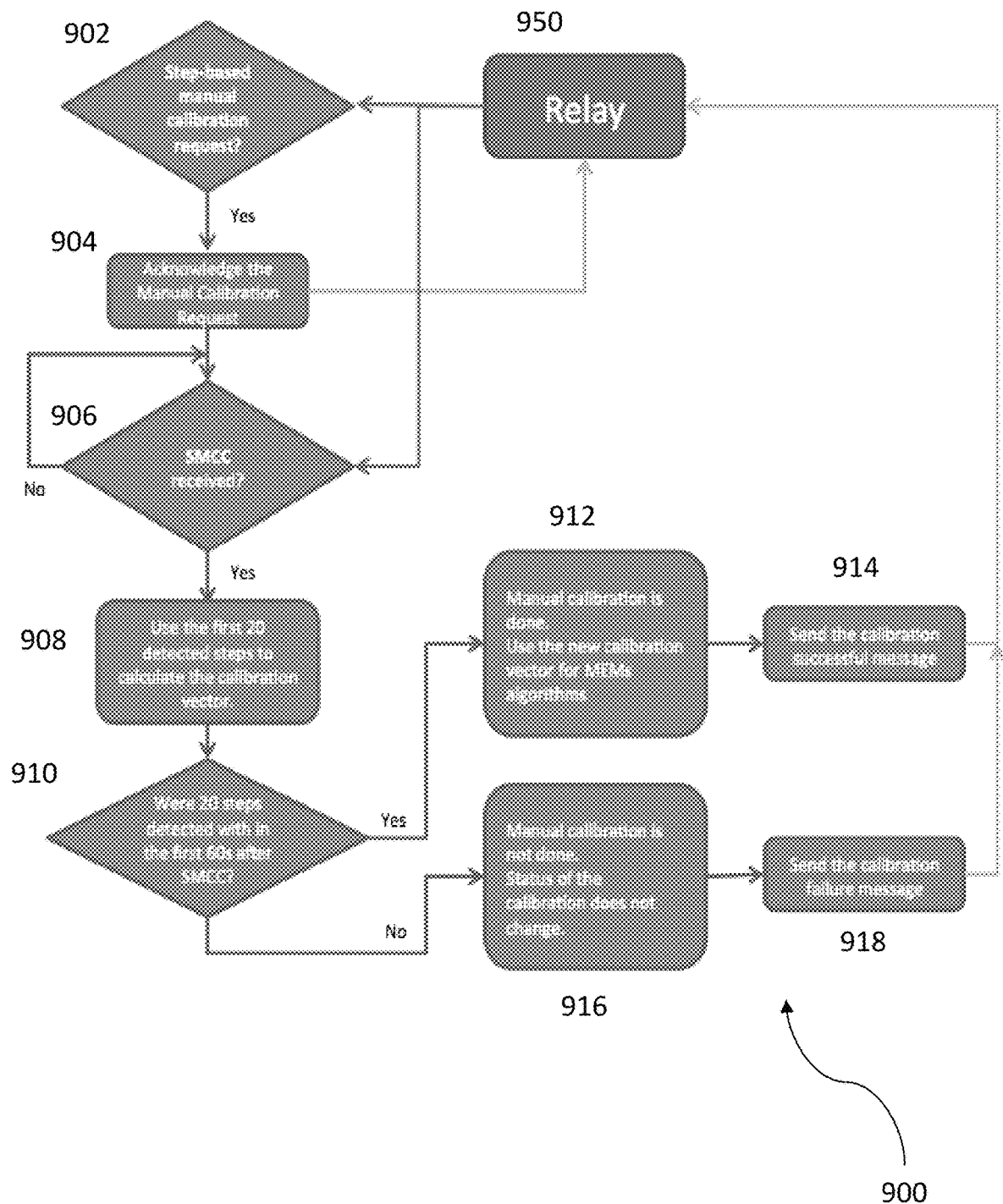
FIG. 9 illustrates a method for manual calibration based on walking in accordance with an embodiment.

The New Upright Calibration Vector determined from FIGS. 8 and 9 represents the vertical calibration vector utilized to generate a rotation matrix. In the case of a bedridden subject, the New Leaning Calibration Vector and the New Supine Calibration Vector determined from FIG. 10 are used to generate a vertical calibration vector and a leaning calibration vector that are both utilized to generate a rotation matrix. Once the vertical calibration vector is obtained, the native axes, or the uncalibrated MEMS axes, of the wireless sensor device with embedded accelerometer are rotated to line up with the user's body axes. The rotation matrix is generated with a single upright calibration vector or with the combination of an upright calibration vector and a leaning (forward or backwards) calibration vector.

For the rotation matrix calculation notation, $X_{i,f}$ equals a vector $X_i$ in the frame of reference f, $R_{n,m}$ is the rotation matrix converting from frame of reference n to frame of reference m, $X_{i,j}$, $Y_{i,i}$, and $Z_{i,i}$ are the basis accelerometer axes in frame i where $X_{i,i}=[1\ 0\ 0]^T$, $Y_{i,i}=[0\ 1\ 0]^T$, $Z_{i,i}=[0\ 0\ 1]^T$, and $C_{VT}$, $C_{lean}$, $C_{SP}$ are the calibration vectors for vertical, leaning, and supine positions respectively. After calculation, the final body axes is represented by X-axis ($X_B$): pointing to the right, Y-axis ($Y_B$): pointing inferiorly (towards feet), and Z-axis ($Z_B$): pointing anteriorly (forward from chest).

Figure 11:
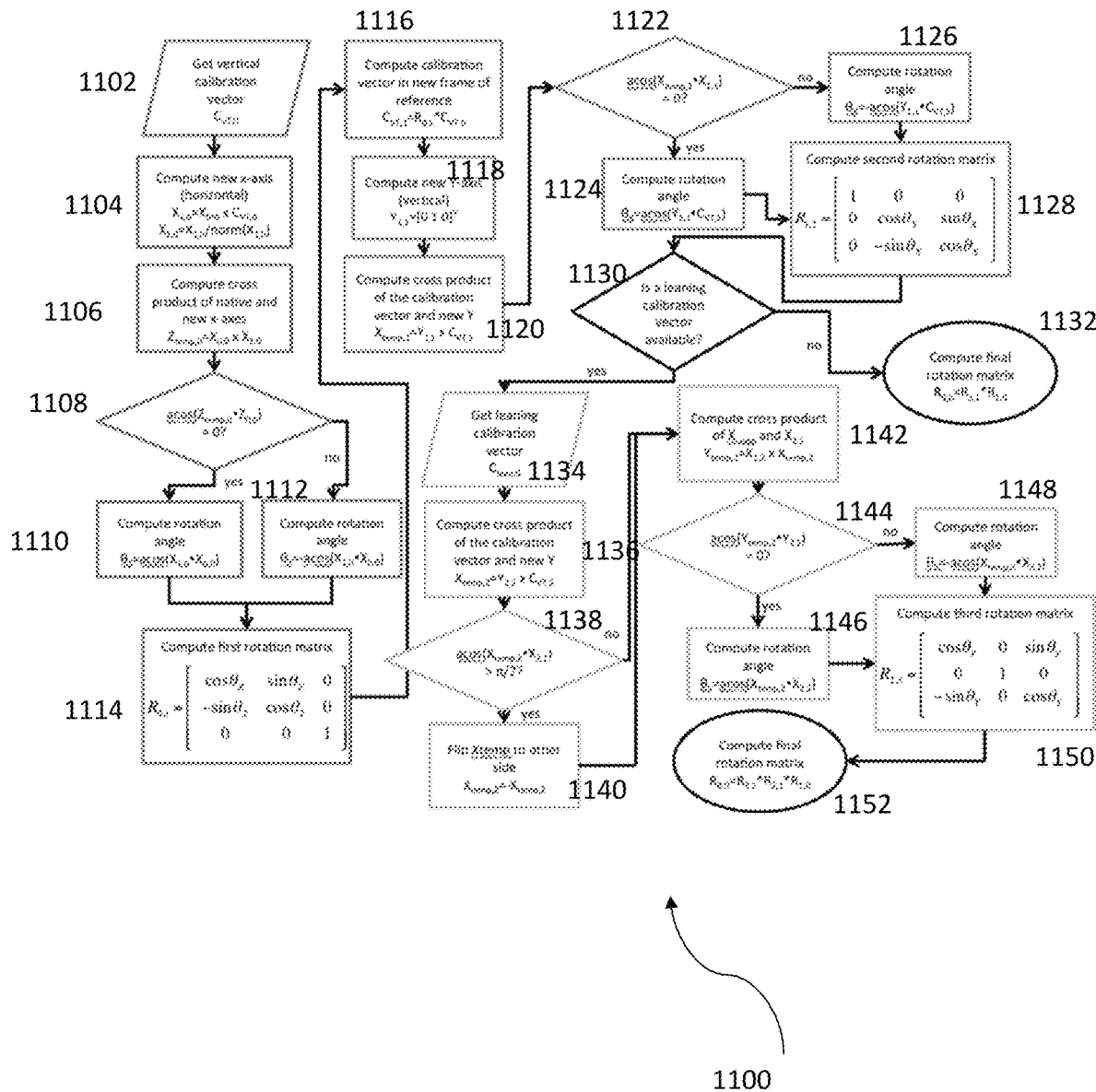
FIG. 11 illustrates a method for calculating a rotation matrix in accordance with an embodiment.

FIG. 11 illustrates a method 1100 for calculating a rotation matrix in accordance with an embodiment. In the method 1100, steps 1102-1114 represent a first section of a rotation matrix algorithm that rotates the native wireless sensor device's accelerometer axes to line up the X-axis ($X_{0,0}$) with the horizontal plane (some combination of medial-lateral ML and anterior-posterior AP); steps 1116-1128 represent a second section of the rotation matrix algorithm that rotates the native accelerometer axes to line up the Y-axis ($Y_{1,1}$) to the body axis VT ($Y_B$); and steps 1134-1150 represent a third section of the rotation matrix algorithm that rotates the X-axis ($X_{2,2}$) to align with the body axis ML ($X_B$) and that rotates the Z-axis ($Z_{2,2}$) to align with the body axis AP ($Z_B$), if an additional leaning calibration vector is provided.

The first and second sections are carried out by the wireless sensor device as long as a VT calibration vector is initially determined via step 1102. The third section requires a leaning calibration vector input to also be provided and results in exact calculations of ML and AP. If the leaning calibration vector input is not provided, the wireless sensor device only determines an approximation of ML and AP because the X-axis and Z-axis are aligned horizontally but not aligned with the actual body axes.

In the method 1100, the wireless sensor device determines a vertical calibration vector ($C_{VT,0}$) in accordance with one of the aforementioned manual calibration procedures described by FIG. 8-10, via step 1102. The wireless sensor device calculates a new horizontal X-axis ($X_{1,0}$) per the equations $X_{1,0}=X_{0,0}*C_{VT,0}$ and $X_{1,0}=X_{1,0}/\text{norm}(X_{1,0})$, via step 1104. The wireless sensor device calculates a cross product ($Z_{temp,0}$) of the native and the new X-axis per the equation $Z_{temp,0}=X_{0,0}\times X_{1,0}$, via step 110B, and then determines whether a $\cos(Z_{temp,0}*Z_{0,0})=0$, via step 1108.

If yes (a $\cos(Z_{temp,0}*Z_{0,0})=0$), then the wireless sensor device calculates a rotation angle per the equation $\theta_Z=a\cos(X_{1,0}\cdot X_{0,0})$, via step 1110, and if no (a $\cos(Z_{temp,0}*Z_{0,0})$ does not equal 0), then the wireless sensor device calculates a rotation angle per the equation $\theta_Z=a\cos(X_{1,0}\cdot X_{0,0})$, via step 1112.

The wireless sensor device calculates a first rotation matrix ($R_{0,1}$) per the equation $$R_{0,1} = \begin{bmatrix} \cos\theta_Z & \sin\theta_Z & 0 \\ -\sin\theta_Z & \cos\theta_Z & 0 \\ 0 & 0 & 1 \end{bmatrix},$$

via step 714, which completes the first section of the rotation matrix algorithm. To begin the second section of the rotation matrix algorithm, the wireless sensor device calculates a calibration vector in a new frame of reference per the equation $C_{VT,1}=R_{0,1}*C_{VT,0}$, via step 1116, and calculates a new vertical Y-axis per the equation $Y_{1,1}=[0\ 1\ 0]^T$, via step 1118. After these two computations, the wireless sensor device calculates a cross product ($X_{temp,1}$) of the calibration vector $C_{VT,1}$ and the new Y-axis $Y_{1,1}$ per the equation $X_{temp,1}=Y_{1,1}\times C_{VT,1}$, via step 1120.

The wireless sensor device determines whether a $\cos(X_{temp,1}*X_{1,1})=0$, via step 1122. If yes (a $\cos(X_{temp,1}*X_{1,1})=0$), then the wireless sensor device calculates a rotation angle per the equation $\theta_X=a\cos(Y_{1,1}\cdot C_{VT,1})$, via step 1124, and if no (a $\cos(X_{temp,1}*X_{1,1})$ does not equal 0), then the wireless sensor device calculates a rotation angle per the equation $\theta_X=-a\cos(Y_{1,1}\cdot C_{VT,1})$, via step 1126. The wireless sensor device calculates a second rotation matrix ($R_{1,2}$) per the equation $$R_{1,2} = \begin{bmatrix} 1 & 0 & 0 \\ 0 & \cos\theta_X & \sin\theta_X \\ 0 & -\sin\theta_X & \cos\theta_X \end{bmatrix},$$

via step 1128, which completes the second section of the rotation matrix algorithm.

The wireless sensor device then determines whether a leaning calibration vector is available, via step 1130. If no, the rotation matrix algorithm ends with the wireless sensor device computing a final rotation matrix ($R_{B,0}$) per the equation $R_{B,0}=R_{2,1}*R_{1,0}$, via step 1132. If yes (a leaning calibration vector is available for the wireless sensor device to utilize), then the third section of the rotation matrix algorithm is initiated with the wireless sensor device obtaining the leaning calibration vector ($C_{lean,0}$), via step 1134.

The wireless sensor device calculates a cross product of the calibration vector and the new Y-axis per the equation $X_{temp,2}=Y_{2,2}\times C_{VT,2}$, via step 1136. If a $\cos(X_{temp,2}\cdot X_{2,2})$ is determined to be more than $\pi/2$, via step 1138, then the wireless sensor device flips $X_{temp}$ to the other side per the equation $X_{temp,2}=-X_{temp,2}$, via step 1140 The wireless sensor device calculates a cross product ($Y_{temp,2}$) of $X_{temp,2}$ and $X_{2,2}$ per the equation $Y_{temp,2}=X_{2,2}\times X_{temp,2}$, via step 1142, and determines whether a $\cos(Y_{temp,2}\cdot Y_{2,2})=0$, via step 1144. If yes (a $\cos(Y_{temp,2}\cdot Y_{2,2})=0$), then the wireless sensor device calculates a rotation angle per the equation $\theta_Y=a\cos(X_{temp,2}\cdot X_{2,2})$, via step 1146, and if no (a $\cos(Y_{temp,2}\cdot Y_{2,2})$ does not equal 0), then the wireless sensor device calculates a rotation angle per the equation $\theta_Y=-a\cos(X_{temp,2}\cdot X_{2,2})$, via step 1148.

After computing the rotation angle, the wireless sensor device calculates a third rotation matrix ($R_{2,3}$) per the equation $$R_{2,3} = \begin{bmatrix} \cos\theta_Y & 0 & \sin\theta_Y \\ 0 & 1 & 0 \\ -\sin\theta_Y & 0 & \cos\theta_Y \end{bmatrix},$$

via step 1150, and calculates the final rotation matrix ($R_{B,0}$) per the equation $R_{B,0}=R_{3,2}*R_{2,1}*R_{1,0}$, via step 1152 to conclude the rotation matrix algorithm.

In one embodiment, if the calibration vectors determined by or provided to the wireless sensor device are not the upright and leaning calibration vectors, but are instead the supine and leaning calibration vectors, the upright calibration vector (VT) is derived by the wireless sensor device.

In one embodiment, during the calibration for bedridden subjects, the supine and leaning calibration vectors are obtained, but a vertical and leaning vector are required for generating the rotation matrix. The vertical calibration vector VT is derived from the supine and leaning calibration vectors. The wireless sensor device determines the upright calibration vector VT by taking the cross product of the supine ($C_{SP}$) and leaning ($C_{lean}$) calibration vectors to calculate a horizontal vector ($C_{horz}$) per the equation $C_{horz}=C_{lean}\times C_{SP}$, taking the cross product of the horizontal and supine calibration vectors to calculate a vertical calibration vector ($C_{VT}$) per the equation $C_{VT}=C_{SP}\times C_{horz}$. At this point, the rotation matrix algorithm described by FIG. 11 is utilized with $C_{VT}$ as the vertical calibration vector and $C_{SP}$ as the leaning calibration vector.

In one embodiment, the wireless sensor device in a patch form-factor is used only during a sleep study where periods of upright positioning are rare or not captured. In this embodiment, the calibration is achieved via a sleep study algorithm using only sleep data with the assumptions that the user is lying on his/her back for most of the period of data collection, the user is supine for some period of the night, the user is in at least two of the other lying subpostures (left lateral, right lateral, prone) for some period of the night, and the patch is worn on the front of the user's chest.

During periods of inactivity, the wireless sensor device utilizes the sleep study algorithm to determine a gravity vector for every predetermined number of seconds (N). A plane is fit such that all of the gravity vectors lie in the plane and the normalization of the plane is the vertical calibration vector VT. The supine calibration vector position $C_{SP}$ is found utilizing the sleep study algorithm and serves as the leaning calibration vector and a rotation matrix is calculated from these two calibration vectors VT and $C_{SP}$.

Figure 12:
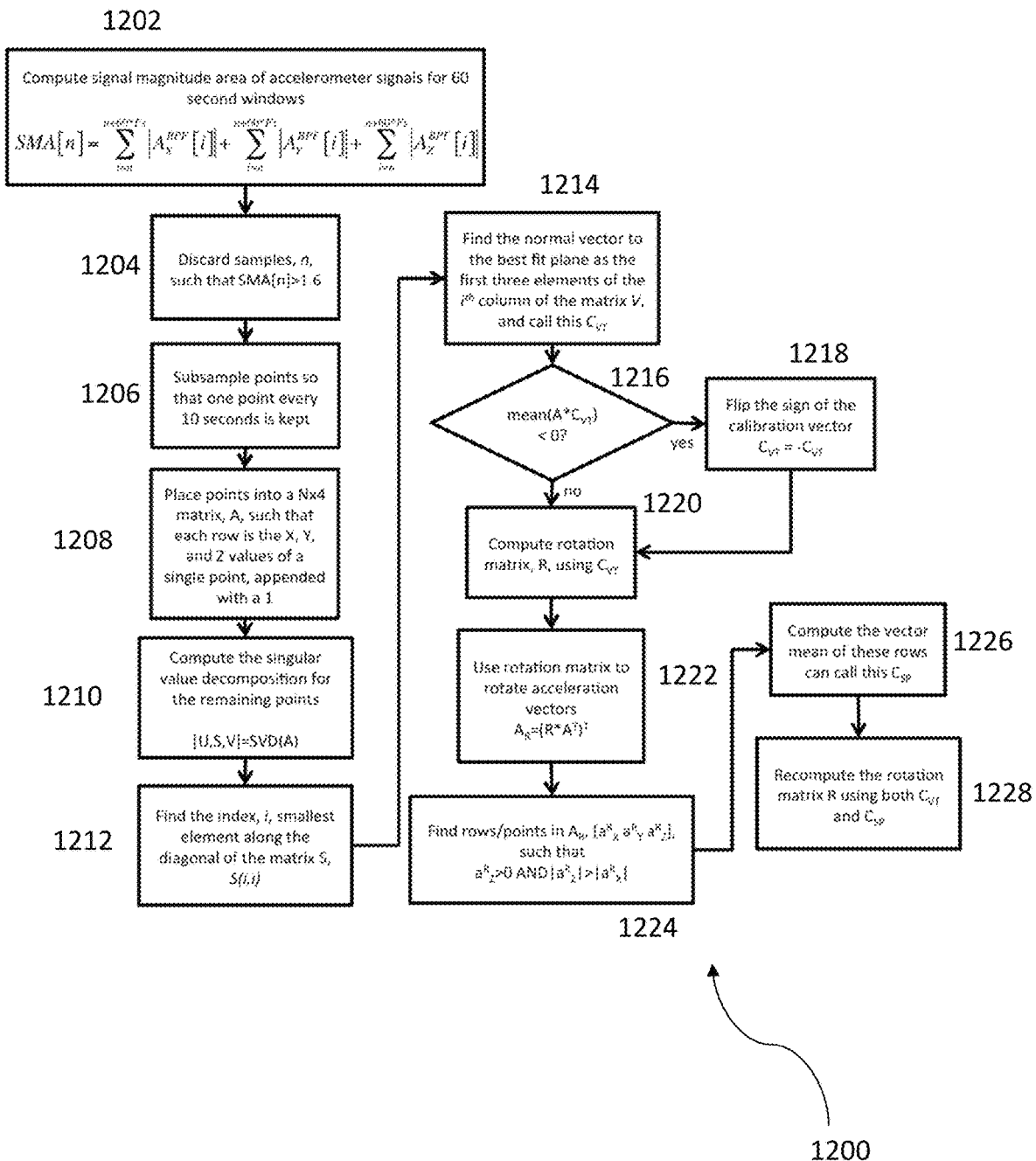
FIG. 12 illustrates a method for calculating a rotation matrix using data from a sleep study in accordance with an embodiment.

FIG. 12 illustrates a method 1200 for calculating a rotation matrix using a sleep study algorithm in accordance with an embodiment. In the method 1200, a wireless sensor device calculates a signal magnitude area of accelerometer signals for 60 second windows per the equation:

$$SMA[n] = \sum_{i=n}^{n+60*Fs} |A_X^{BPF}[i]| + \sum_{i=n}^{n+60*Fs} |A_Y^{BPF}[i]| + \sum_{i=n}^{n+60*Fs} |A_Z^{BPF}[i]|,$$

via step 1202.

The wireless sensor device discards samples, n, such that SMA[n]>1.6, via step 1204, and subsamples points so that one point every 10 seconds is kept, via step 1206. Using singular value decomposition (SVD), the wireless sensor device calculates a best fit plane and normalizes the vector $C_{VT}$ by placing points into a N×4 matrix, A, such that each row is the X, Y, and Z values of a single point, appended with a 1, via step 1208. The SVD is calculated for the remaining points per the equation [U,S,V]=SVD(A), via step 1210 and the index, i, is found as the smallest element along the diagonal of the matrix S per S(i,i), via step 1212. The wireless sensor device determines a normal vector to the best fit plane as the first three elements of the $i^{th}$ column of the matrix V which represents $C_{VT}$, via step 1214.

At this point, it is unknown whether $C_{VT}$ is pointing towards the user's head or feet and so the wireless sensor device determines if a mean of the point projections is positive or negative per the equation mean(A*$C_{VT}$)<0, via step 1216, and flips the sign if necessary, via step 1218. The wireless sensor device calculates a rotation matrix R using $C_{VT}$, via step 1220, and uses the rotation matrix to rotate the acceleration vectors per the equation $A_R=(R*A^T)^T$ to find points that correspond to the supine calibration vector, via step 1222. The wireless sensor device determines the rows/points in $A_R$, $[a^R_X a^R_Y a^R_Z]$, such that $a^R_Z>0$ and $|a^R_Z|>|a^R_X|$, via step 1224 and computes the vector mean of these rows to find the supine calibration vector $C_{SP}$, via step 1226. To conclude the sleep study algorithm, the rotation matrix R is recalculated by the wireless sensor device using both the newly determined $C_{VT}$ and $C_{SP}$.

Figure 13:
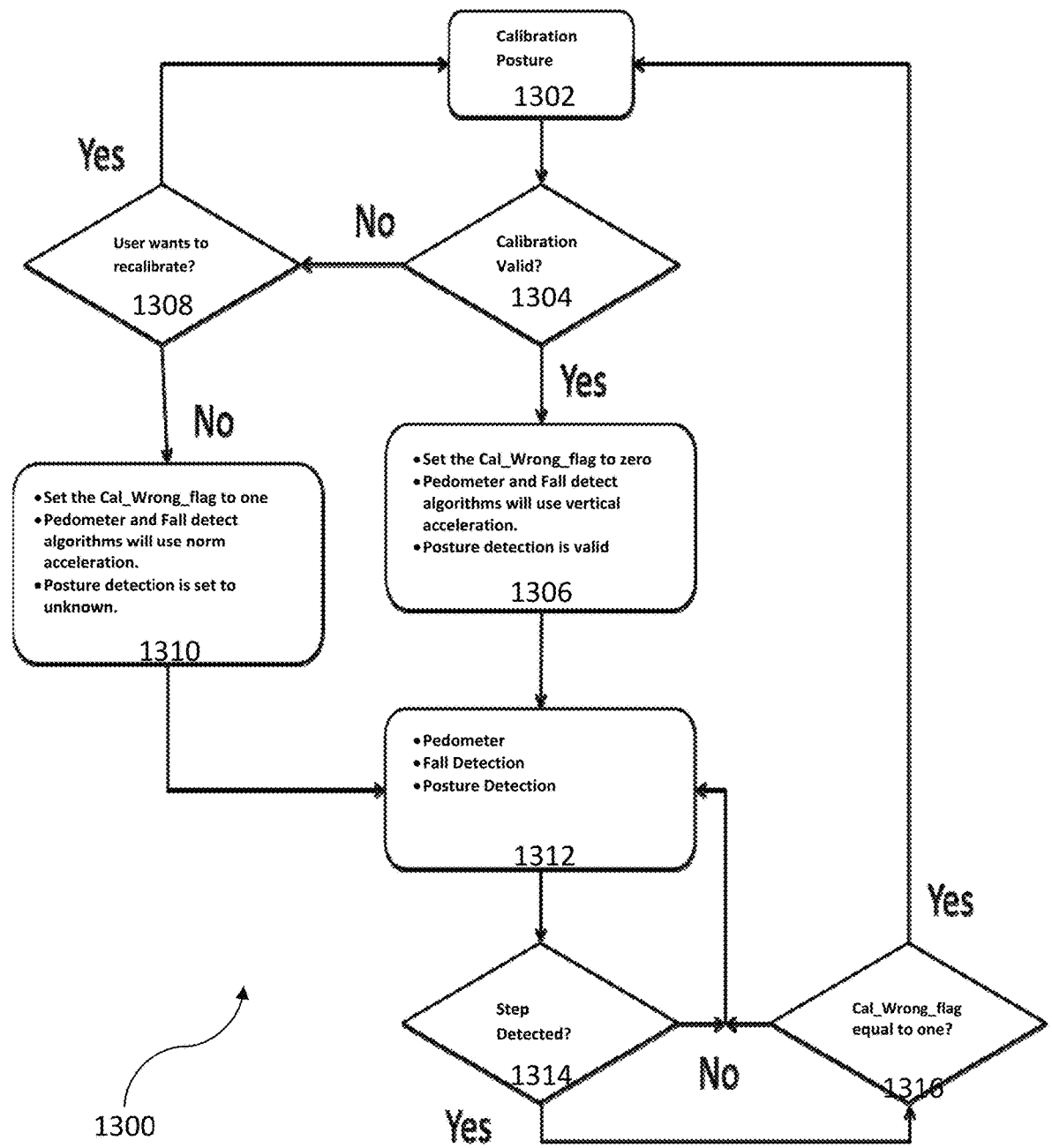
FIG. 13 illustrates a method for calibration validation in accordance with an embodiment.

Additional Calibration Techniques:

FIG. 13 illustrates a method 1300 for calibration validation in accordance with an embodiment. The wireless sensor device is attached to a user in any orientation and on any bodily location of the user. Referring to FIGS. 4 and 13 together, the method 1300 comprises an explicit calibration of the user's posture to determine a calibration vector, via step 1302. In one embodiment, calibrating the user's posture explicitly includes but is not limited to the user notifying the wireless sensor device 400 when the user is in a vertical position and the wireless sensor device 400 being attached to the user's chest when the user is in a vertical position.

In this embodiment, the user notifies the wireless sensor device 400 in a variety of ways including but not limited to tapping the wireless sensor device 400, selecting a button of the wireless sensor device 400, and interacting with a mobile application interface of the wireless sensor device 400. Furthermore, in this embodiment, when the wireless sensor device 400 is attached to the user's chest while the user is in a vertical position, the wireless sensor device 400 recognizes contact impedance to confirm attachment between the user and the wireless sensor device 400.

The wireless sensor device 400 checks to see whether the explicitly determined calibration vector is valid, via step 1304. If the determined calibration vector is valid, the wireless sensor device 400 sets cal_wrong_flag to zero (0), uses a vertical acceleration based on the validated calibration vector in both pedometer activity and fall detection algorithms, and confirms posture detection is valid, via step 1306.

In FIG. 13, if the explicitly determined calibration vector is not valid, the wireless sensor device 400 displays a validation failure message to the user prompting the user to determine whether the user wants to explicitly recalibrate another calibration vector, via step 1308. If the user wants to explicitly recalibrate another calibration vector, the method 1300 returns back to step 1302. If the user does not want to explicitly recalibrate another calibration vector, the method 1300 sets cal_wrong_flag to one (1), uses a norm of acceleration in both pedometer activity and fall detection algorithms, and sets posture detection to unknown, via step 1310. In this embodiment, when the determined calibration vector is not valid, the wireless sensor device 1300 monitors the activity of the user using a set of algorithms that are independent of the calibration vector.

In one embodiment, the determined calibration vector is checked for validity by ensuring a magnitude of acceleration along an anteroposterior axis of the user is less than a predetermined threshold including but not limited to g*sin (π/6), where g is the acceleration due to gravity. In this embodiment, if the magnitude of acceleration along the anteroposterior axis of the user is less than the predetermined threshold, then the calibration vector is determined to be valid and the method 1300 proceeds to step 1306. However, if the magnitude of acceleration along the anteroposterior axis of the user is greater than or equal to the predetermined threshold, then the calibration vector is determined to be invalid and the method 1300 proceeds to step 1308. The anteroposterior axis of the user measures the axis from the front chest to the back of the user and is nearly perpendicular to gravity when the user is in a vertical posture.

Figure 14:
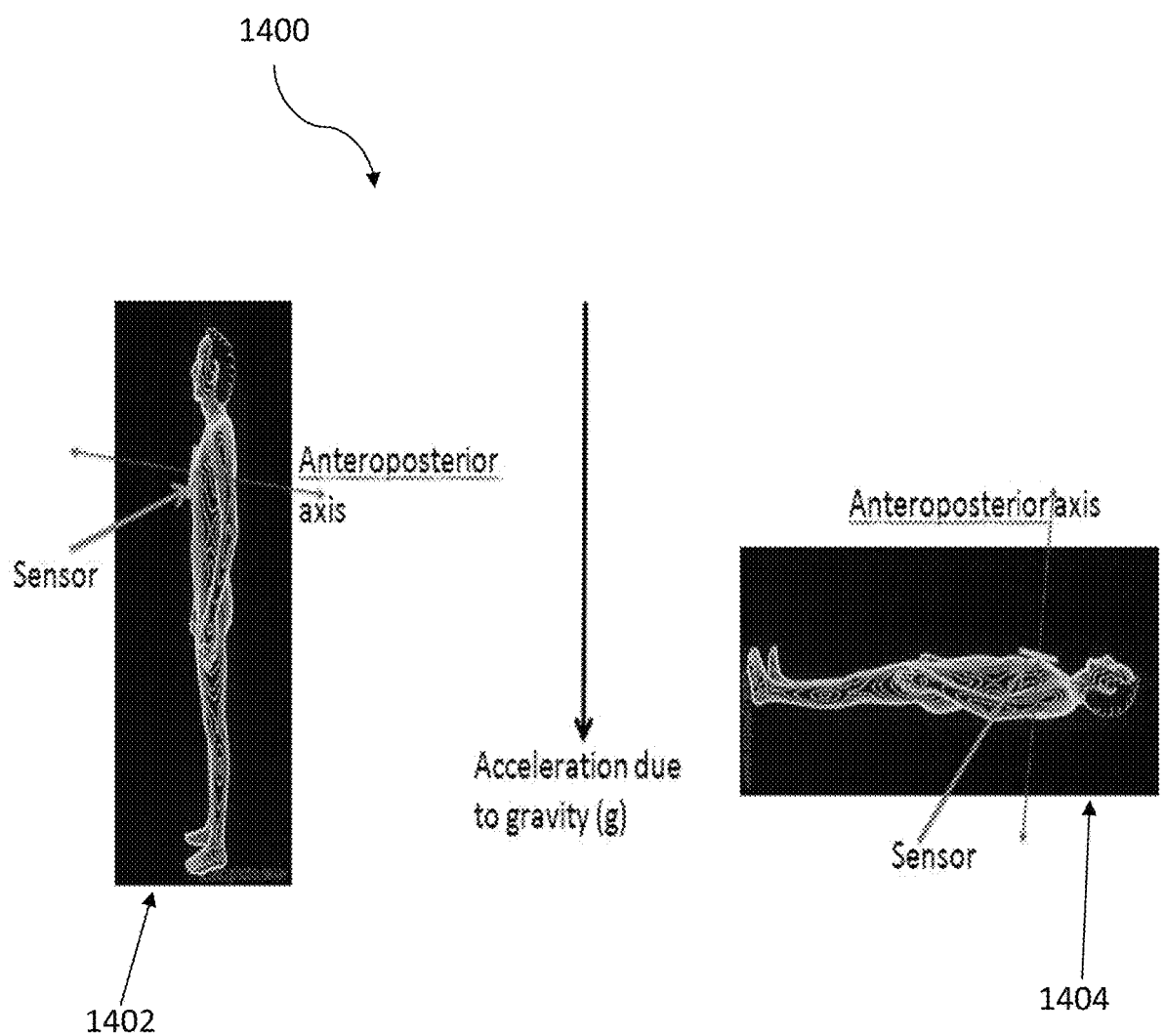
FIG. 14 illustrates a diagram of calibration vector checking in accordance with an embodiment.

FIG. 14 illustrates a diagram 1400 of calibration vector checking in accordance with an embodiment. The diagram 1400 includes a first scenario 1402 where the calibration check passes because an absolute value of acceleration along the anteroposterior axis of the user is less than the predetermined threshold. The diagram 1400 includes a second scenario 1404 where the calibration check fails because an absolute value of acceleration along the anteroposterior axis of the user is greater than or equal to the predetermined threshold.

Referring back to FIG. 13, after both steps 1310 and 1306, the user's activity including but not limited to pedometer activity, fall detection, and posture detection is monitored using various algorithms depending upon whether the calibration vector is validated or not, via step 1312. In one embodiment, monitoring the activity of the user using the validated calibration vector includes but is not limited to monitoring pedometer activity using a vertical component of an acceleration vector of the user, monitoring fall detection using p-norm of the acceleration vector to detect an impact and an angle of the acceleration vector with respect to the validated calibration vector thereby determining a horizontal position of the user after impact, and monitoring posture detection using both the acceleration vector and the validated calibration vector.

In another embodiment, monitoring the activity of the user using a non-validated calibration vector due to a validation failure includes but is not limited to monitoring pedometer activity using 2-norm of an acceleration vector of the user and monitoring fall detection using p-norm of the acceleration vector to detect an impact. In this embodiment, the monitoring of fall detection does not calculate an angle and the posture of the user is unknown. Accordingly, it is desirable to monitor the activity of the user using a validated calibration vector.

Therefore, the activity algorithms utilized by the wireless sensor device 400 vary when using a validated calibration vector and when not using a validated calibration vector. In one embodiment, current acceleration (a) and calibration vectors (c) are utilized by the wireless sensor device 400 in the activity algorithms with a=(ax, ay, az) and c=(cx, cy, cz) when the calibration vector is validated.

In this embodiment, the activity algorithms that include a validated calibration vector comprise a pedometer activity algorithm that is based on a vertical component of the acceleration vector (pedometer activity (v)=a·c=ax*cx+ay*cy+az*cz), a fall detection algorithm that is based on p-norm of a to detect an impact and angle of a with respect to c to determine a horizontal position of the user after impact (p-norm of a=($|ax|^p+|ay|^p+|az|^p$)^(1/p), for p>=1; angle of a calculated using a·c and 2-norms of a and c), and a posture detection algorithm that is based on a·c, cz and az.

Furthermore, in another embodiment, the activity algorithms that are utilized by the wireless sensor device 400 when not using a validated calibration vector include but are not limited to a pedometer activity algorithm that is based on 2-norms of a, a fall detection algorithm that is based on p-norm of a to detect an impact where no angle of a is calculated, and no posture detection algorithm because the posture of the user is unknown.

In the method 1300, once footsteps of the user are detected by a pedometer type device that has been integrated into the wireless sensor device 400, via step 1314, the wireless sensor device 400 utilizes implicit calibration to determine a new calibration vector. In one embodiment, the implicit calibration includes but is not limited to the wireless sensor device 400 deriving a vertical position based on an acceleration vector corresponding to footsteps when the user is walking. After the implicit calibration, the method 1300 checks to see whether cal_wrong_flag is equal to one (1), via step 1316.

If cal_wrong_flag is equal to one (1) indicating that the wireless sensor device 400 has been monitoring the activity of the user using a non-validated calibration vector, the method 1300 returns back to step 1302 to validate the new calibration vector. If cal_wrong_flag is not equal to one (1), indicating that the wireless sensor device 400 has been monitoring the activity of the user using a validated calibration vector, the method 1300 returns back to step 1312 and the wireless sensor device 400 continues the activity monitoring of the user.

Figure 15:
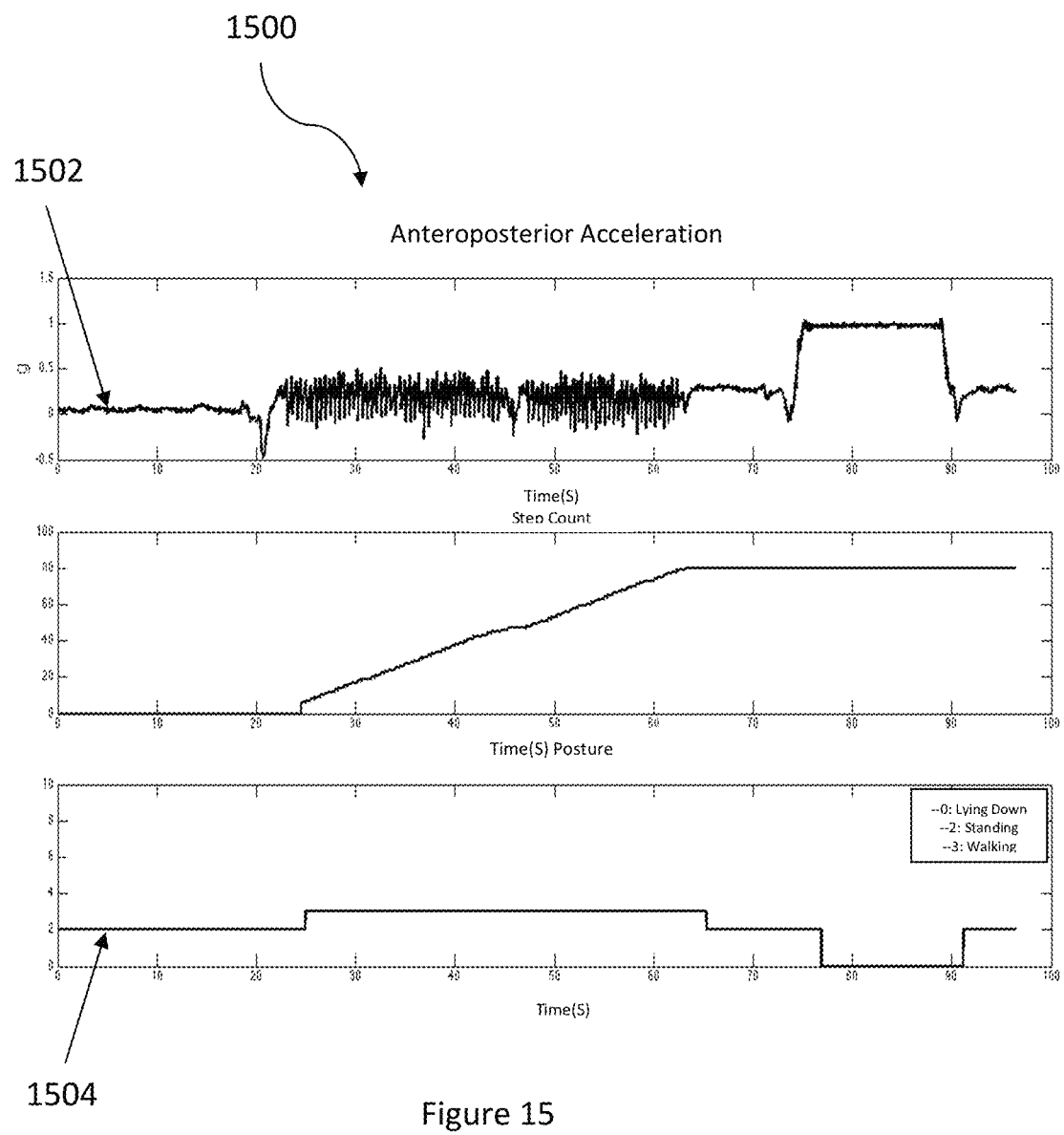
FIG. 15 illustrates a diagram of an example of explicit calibration in accordance with an embodiment.

FIG. 15 illustrates a diagram 1500 of an example of explicit calibration in accordance with an embodiment. The diagram 1500 plots anteroposterior acceleration, step count, and posture of the user over a predetermined time period. The diagram 1500 starts with a valid explicit calibration 1502 corresponding to a known standing posture 1504 of the user. The explicit calibration is valid because the user is in a standing posture when the user has notified the wireless sensor device to explicitly calibrate or the wireless sensor device has been attached to the user while in a standing posture.

As the step count of the user increases, the anteroposterior acceleration fluctuates and the posture of the user is identified to be in a walking posture. At approximately sixty (60) seconds, the step count of the user doesn't increase anymore thereby illustrating another change in the user's posture.

Figure 16:
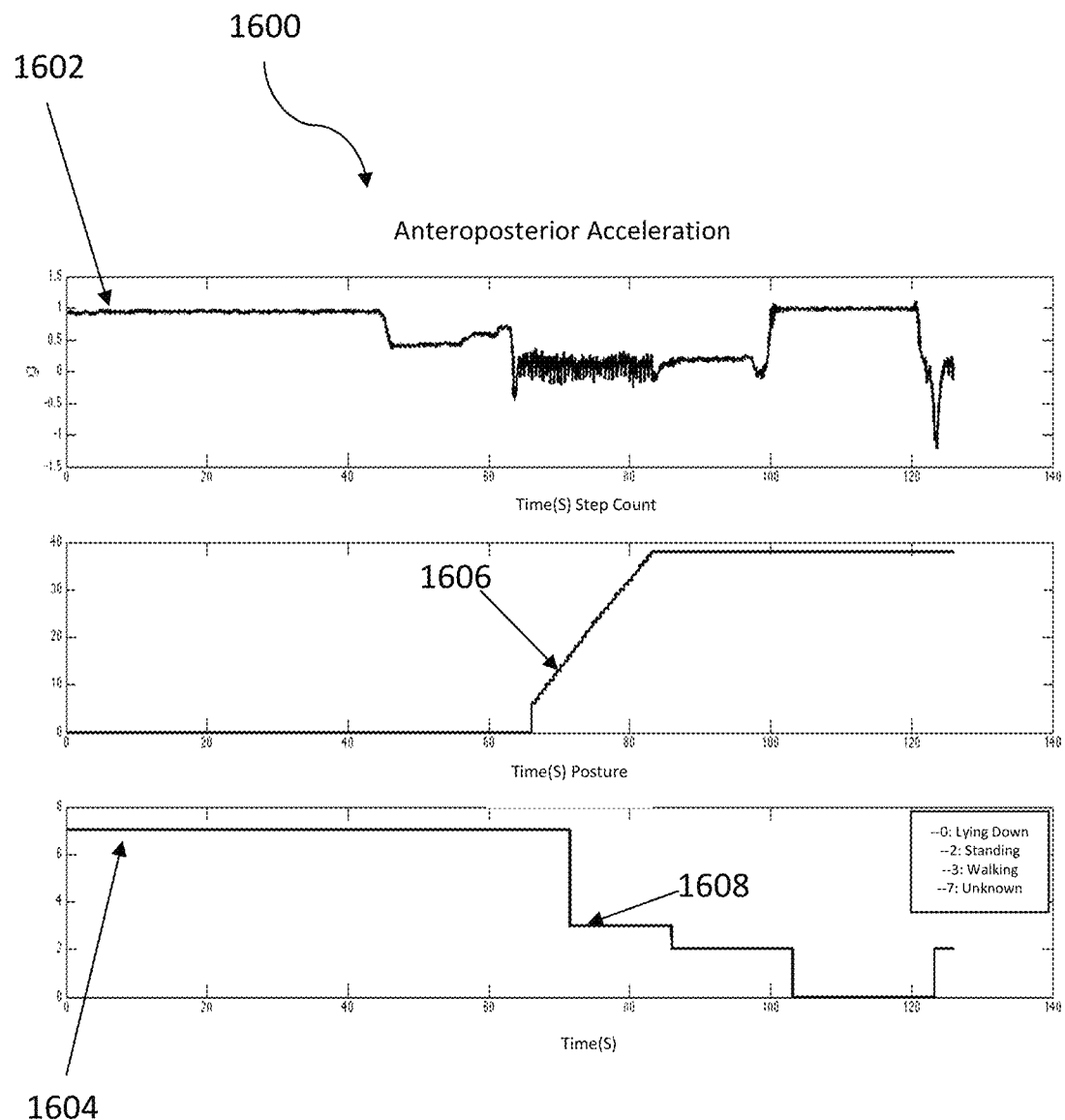
FIG. 16 illustrates a diagram of an example of implicit calibration in accordance with an embodiment.

FIG. 16 illustrates a diagram 1600 of an example of implicit calibration in accordance with an embodiment. The diagram 1600 plots anteroposterior acceleration, step count, and posture of the user over a predetermined time period. The diagram 1600 starts with an invalid explicit calibration 1602 corresponding to an unknown posture 1604 of the user. The explicit calibration is invalid because the user is in an unknown posture when the user has notified the wireless sensor device to explicitly calibrate or the wireless sensor device has not been attached to the user while in a standing posture.

As aforementioned, due to this invalid explicit calibration, the wireless sensor device attached to the user will monitor the user's activity by utilizing activity algorithms that do not incorporate a calibration vector. As the step count of the user increases, implicit calibration while walking 1606 occurs to incorporate a newly determined calibration vector into the activity algorithms utilized by the wireless sensor device. At this time while the user is walking, which is at approximately seventy (70) seconds, the wireless sensor device calculates a known posture of the user 1608.

As above described, the method and system allow for calibration of a chest-mounted wireless sensor device for posture and activity detection of a user. By implementing at least an accelerometer within a wireless sensor device to detect acceleration and posture samples and an application located on the wireless sensor device to process the detected acceleration and posture samples, and calibrating the wireless sensor device using a variety of automatic and manual calibration methodologies, an efficient and cost-effective calibration system is achieved that can support various types of activities and can confirm changes in a user's posture.

A method and system for calibration of a chest-mounted wireless sensor device for posture and activity detection of a user have been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk.

Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method to calibrate a wireless sensor device, the method comprising:
   transmitting a signal to a relay device;
   in response to a determination, by the relay device, that the wireless sensor device is within a predetermined proximity from the relay device based on the transmitted signal, communicatively connecting the wireless sensor device to the relay device, and receiving a manual calibration request from the relay device,
      wherein the determination, by the relay device, that the wireless sensor device is within a predetermined proximity from the relay device is based on:
         a first determination, by the relay device, of a signal index from the transmitted signal,
         a second determination, by the relay device, of a threshold value for the signal index,
         a third determination, by the relay device, that the signal index equals or exceeds the threshold value;
   determining a vertical calibration vector using a manual calibration; and
   determining a rotation matrix using the determined vertical calibration vector to line up native axes of the wireless sensor device with body axes,
   wherein the manual calibration request includes one of: an upright manual calibration request, a walking manual calibration request, or a bedridden user manual calibration request,
   wherein in response to the received manual calibration request is an upright manual calibration request, the determining the vertical calibration vector using the manual calibration includes:
      detecting a microelectromechanical systems (MEMS) based vertical calibration vector;
      filtering the MEMS based vertical calibration vector using a lowpass filter;
      replacing a current upright vertical calibration vector with the filtered MEMS based vertical calibration vector; and
      transmitting a status message to the relay device,
   wherein in response to the received manual calibration request is the walking manual calibration request, the determining the vertical calibration vector using the manual calibration includes:
      calculating a microelectromechanical systems (MEMS) based vertical calibration vector during a user's walking period;
      determining whether the walking period meets a minimum footstep number threshold; and
      transmitting a status message to the relay device, and
   wherein in response to the received manual calibration request is the bedridden user manual calibration request, the determining the vertical calibration vector using the manual calibration includes:
      determining both a supine calibration vector and a leaning calibration vector;
      calculating a microelectromechanical systems (MEMS) based vertical calibration vector based on the supine calibration vector and the leaning calibration vector; and
      transmitting a status message to the relay device.

2. The method of claim 1, wherein the signal index is a received signal strength indicator (RSSI) or a received channel power indicator.

3. The method of claim 1, wherein the status message indicates one of a Manual Calibration Success status or a Manual Calibration Warning status.

4. A wireless sensor device, comprising:
   a processor; and
   a memory coupled to the processor, wherein the memory includes an application that, when executed by the processor, causes the processor to:
   transmit a signal to a relay device;
   in response to a determination, by the relay device, that the wireless sensor device is within a predetermined proximity from the relay device based on the transmitted signal, communicatively connect the wireless sensor device to the relay device, and receive a manual calibration request from the relay device,
      wherein the determination, by the relay device, that the wireless sensor device is within a predetermined proximity from the relay device is based on:
         a first determination, by the relay device, of a signal index from the transmitted signal,
         a second determination, by the relay device, of a threshold value for the signal index,
         a third determination, by the relay device, that the signal index equals or exceeds the threshold value;
   determine a vertical calibration vector using a manual calibration; and
   determine a rotation matrix using the vertical calibration vector to line up native axes of the wireless sensor device with body axes,
   wherein the manual calibration request includes one of: an upright manual calibration request, a walking manual calibration request, or a bedridden user manual calibration request,
   wherein in response to the received manual calibration request is an upright manual calibration request, the determining the vertical calibration vector using the manual calibration includes:
      detecting a microelectromechanical systems (MEMS) based vertical calibration vector;
      filtering the MEMS based vertical calibration vector using a lowpass filter;
      replacing a current upright vertical calibration vector with the filtered MEMS based vertical calibration vector; and
      transmitting a status message to the relay device,
   wherein in response to the received manual calibration request is the walking manual calibration request, the determining the vertical calibration vector using the manual calibration includes:
      calculating a microelectromechanical systems (MEMS) based vertical calibration vector during a user's walking period;
      determining whether the walking period meets a minimum footstep number threshold; and
      transmitting a status message to the relay device, and
   wherein in response to the received manual calibration request is the bedridden user manual calibration request, the determining the vertical calibration vector using the manual calibration includes:

determining both a supine calibration vector and a leaning calibration vector;

calculating a microelectromechanical systems (MEMS) based vertical calibration vector based on the supine calibration vector and the leaning calibration vector; and transmitting a status message to the relay device.

5. The wireless sensor device of claim 4, wherein the signal index is a received signal strength indicator (RSSI) or a received channel power indicator.

\* \* \* \* \*